US006979351B2

(12) United States Patent
Forsell et al.

(10) Patent No.: US 6,979,351 B2
(45) Date of Patent: Dec. 27, 2005

(54) IMPLANTABLE CERAMIC VALVE PUMP ASSEMBLY

(75) Inventors: Peter Forsell, Zug (CH); Leif Granat, Vallingby (SE)

(73) Assignee: Potencia Medical AG, Baar (CH)

( * ) Notice: Subject to any disclaimer, the term of this patent is extended or adjusted under 35 U.S.C. 154(b) by 0 days.

(21) Appl. No.: 10/631,959

(22) Filed: Aug. 1, 2003

(65) Prior Publication Data

US 2004/0098113 A1 May 20, 2004

Related U.S. Application Data

(60) Provisional application No. 60/400,063, filed on Aug. 2, 2002.

(51) Int. Cl.[7] ............................................... A61M 1/10
(52) U.S. Cl. ....................................................... 623/3.1
(58) Field of Search ........................ 623/3.1, 3.11–3.3, 623/9; 417/505, 269, 413.1, 510; 137/625.11, 137/625.15

(56) References Cited

U.S. PATENT DOCUMENTS

| 4,146,029 A | | 3/1979 | Ellinwood, Jr. |
| 4,538,607 A | * | 9/1985 | Saul ...................... 128/207.16 |
| 4,780,064 A | | 10/1988 | Olsen |
| 4,822,341 A | | 4/1989 | Colone |
| 5,531,684 A | | 7/1996 | Ensminger et al. |
| 6,302,910 B1 | * | 10/2001 | Yamazaki et al. ........... 623/3.1 |
| 6,576,010 B2 | * | 6/2003 | Ulert et al. .................. 623/3.1 |

* cited by examiner

*Primary Examiner*—Alvin J. Stewart
(74) *Attorney, Agent, or Firm*—Nixon & Vanderhye P.C.

(57) ABSTRACT

An apparatus for distributing a liquid in a patient's body comprises an implantable pump adapted to pump the liquid and an implantable valve device adapted to direct the liquid pumped by the pump. A first ceramic valve member of the valve device includes a first plane surface and a second ceramic valve member of the valve device includes a second plane surface facing and touching the first plane surface. The second valve member is displaceable relative to the first valve member between different positions, wherein the valve members include different liquid channels. The valve device is operable to displace the second valve member to hydraulically connect the pump to at least one of the liquid channels in at least one of the positions.

139 Claims, 18 Drawing Sheets

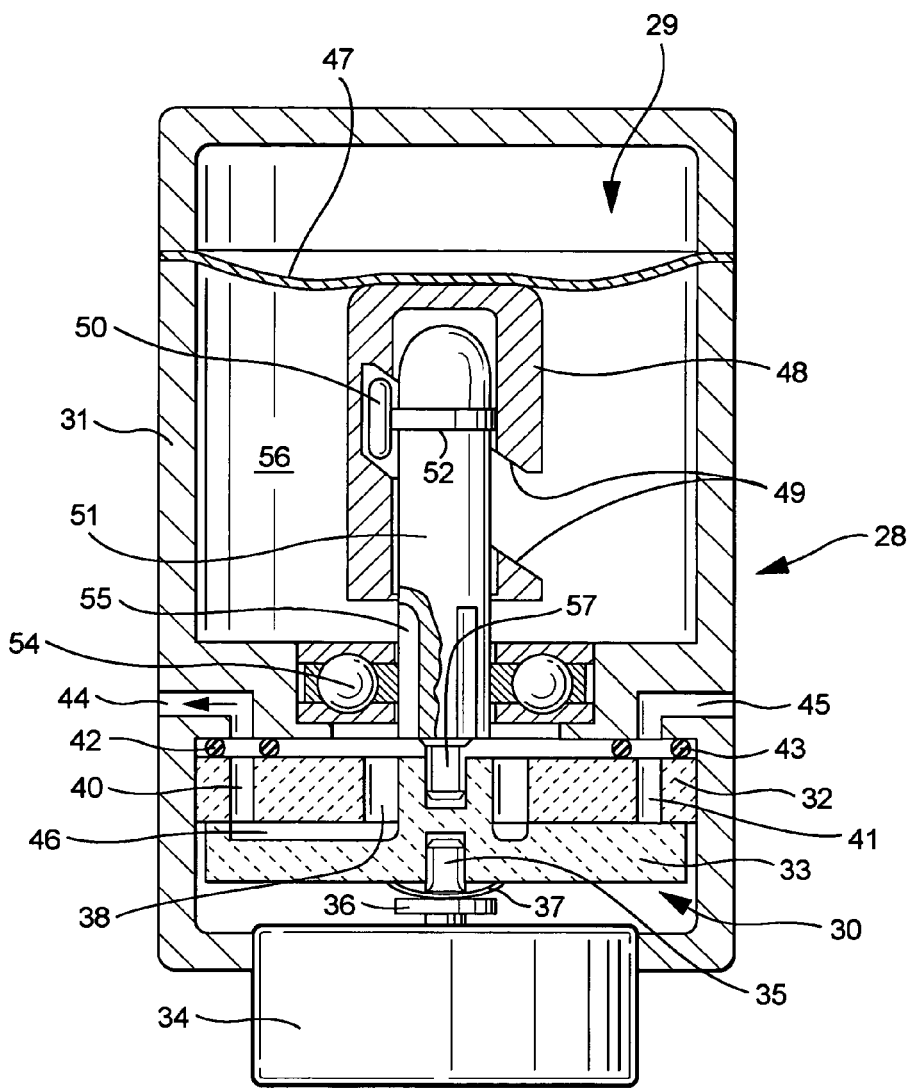
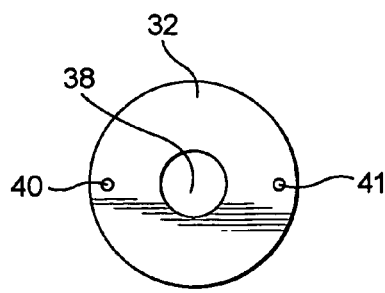
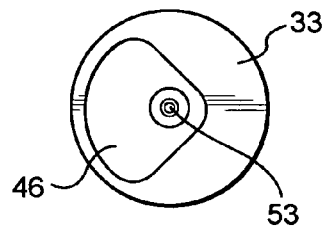
Fig. 5
Fig. 6   Fig. 7

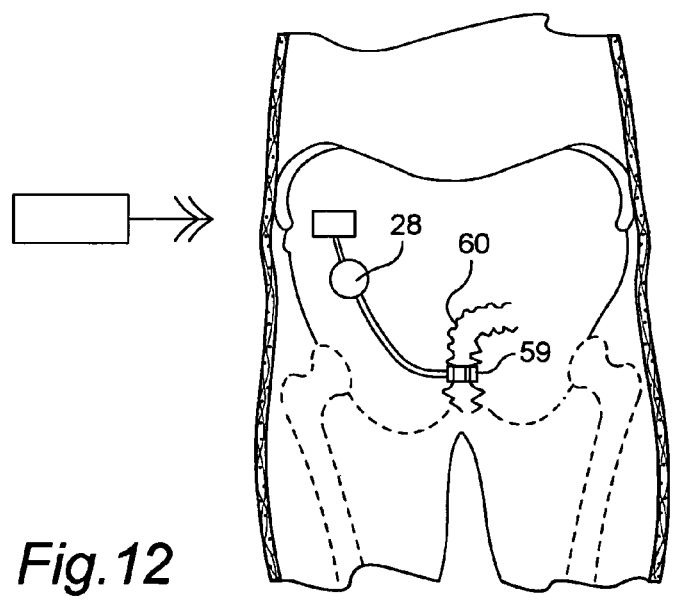
*Fig.12*
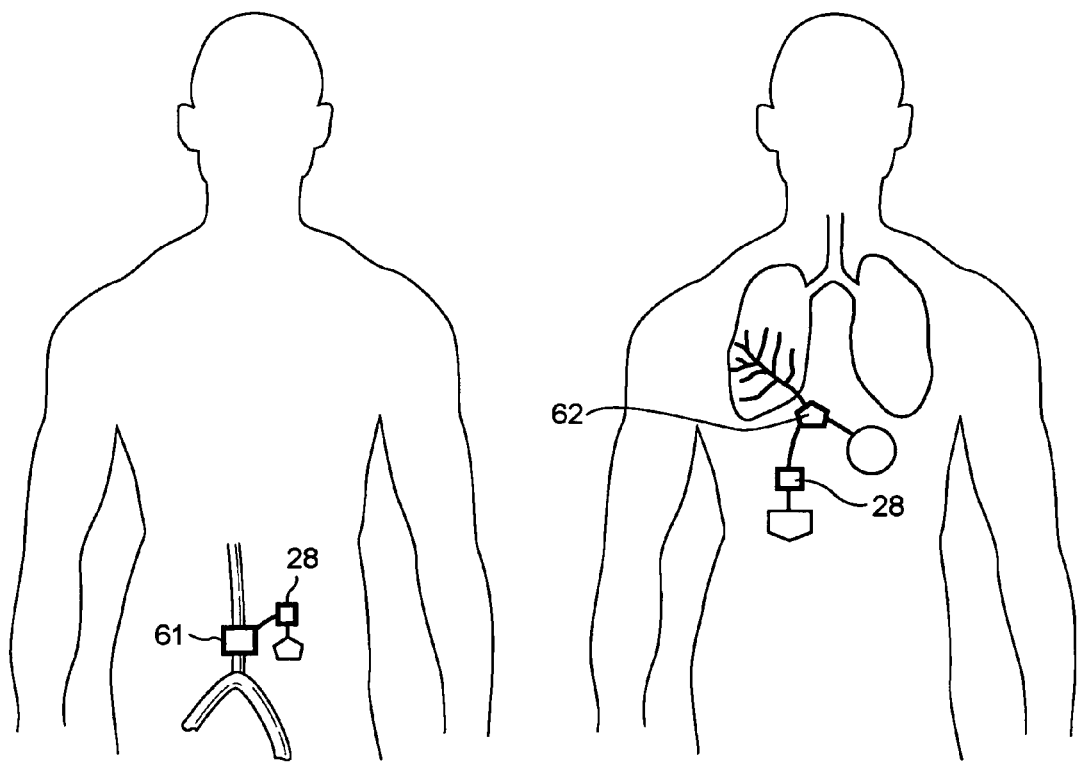
*Fig.13*        *Fig.14*

IMPLANTABLE CERAMIC VALVE PUMP ASSEMBLY

This application claims the benefit of Provisional Application Ser. No. 60/400,063, filed Aug. 2, 2002.

BACKGROUND OF THE INVENTION

The present invention relates to an apparatus for distributing a liquid in a patient's body, wherein the apparatus includes an implantable valve pump assembly for pumping the liquid. The invention also relates to a valve device of the apparatus particularly suited for implantation in the patient's body to direct the liquid. The term "patient" includes a human being or animal.

There are many important requirements for a valve pump assembly that is suited for implantation in the human body. The valve pump assembly should be small, often be capable of generating two to three bars of pressure, have a sufficient flow capacity, sometimes in the order of two to three ml per minute, and, above all, consume little energy so that, for example, an implanted battery powering the assembly will last for a long time. Many of the above requirements are contradictory. Existing small pumps generally have a too low pressure capability, a too low flow capacity and a too high energy consumption to be suited for implantation in a human body.

Another important requirement for an implantable pump, which to some extent is related to the consumption of current, is that the amount of heat that the pump generates during operation should be low. Legally, an implant is not allowed to increase the temperature inside a human body by more than 3° C., ice., from 37° to 40° C. Thus, it is very important that the energy loss of the pump that generates heat be very low.

Another important requirement for an implantable valve pump assembly is that no leakage or diffusion of liquid should occur when the implanted assembly has not been operated for a long period of time. A traditional valve of prior valve pump assemblies, typically a non-return valve, works nicely when pressure is prevailing in the hydraulic channels of the valve. In an implanted valve, however, the pressure can at times be zero, which would make it very difficult to keep the valve properly working over a long period of time. Even more important is the long term diffusion which occurs across nearly all kinds of polymer or plastic material over a long period of time.

A further important requirement for an implantable valve pump assembly is that the pump should be capable of pumping in different directions without risking deterioration of the function of the valve over time. For example, the valve might become clogged or might stop working after not operating for a long period of time in a temperature of 37° C.

SUMMARY OF THE INVENTION

An object of the present invention is to provide a new small reliable valve device suited for implantation in an animal or human body. Another object of the present invention is to provide an apparatus for distributing a liquid in a patient's body, wherein the apparatus includes a small inexpensive reliable valve pump assembly suited for implantation in the patient. Yet another object of the present invention is to provide an apparatus for distributing a liquid with an implantable valve pump assembly that operates with low energy loss and low friction, so that insignificant heat from the assembly is dissipated inside the patient's body. Yet another object of the present invention is to provide an apparatus for distributing a liquid with an implantable valve pump assembly that is capable of working for a very long period of time when implanted. Yet another object of the present invention is to provide an apparatus for distributing a liquid with an implantable miniature size valve pump assembly, which is capable of pumping significant volume with significant pressure. Yet another object of the present invention is to provide an apparatus for distributing a liquid with an implantable valve pump assembly that can pump in two different directions and still requires very little current for its operation. Yet another object of the present invention is to provide a valve pump assembly that will work without degrading for a long period of time and without experiencing any problems with diffusion for a long period of time.

Accordingly, in accordance with a first aspect of the present invention, there is provided a valve device, comprising a first valve member including a first plane surface, and a second valve member including a second plane surface facing and touching the first plane surface and being displaceable relative to the first valve member between different positions, the valve members including different liquid channels, wherein the second valve member is adapted to connect at least two of the different channels to each other in at least one of the positions.

The first and second plane surfaces of the valve members are preferably made with smoothness such that they form a liquid seal as they touch each other. As a result, there is no need for any separate sealing means to seal between the different channels.

The valve members are suitably made of a material inert enough to maintain a low friction between the first and second plane surfaces over time, whereby the risk of the smooth plane surfaces members being stuck to each other is eliminated. For example, the valve members may be made of a ceramic material.

Generally, the second plane surface of the second valve member is adapted to slide on the first plane surface of the first valve member, which gives the advantage that the force required to accomplish the displacement of the second valve member can be very weak.

The first valve member may have two separate liquid channels, i.e., first and second channels. In this case, the second valve member is adapted to connect the first and second channels to each other, when the second valve member is in a first position, and to seal the first channel, when the second valve member is in a second position. The separate liquid channels suitably open on the first plane surface of the first valve member, and the second plane surface has an open channel forming a liquid flow connection between the first and second channels, when the second valve member is in the first position.

Alternatively, the first valve member may have at least three separate liquid channels, i.e., first, second and third channels. In this alternative the second valve member is adapted to connect the first and second channels to each other, when the second valve member is in a first position, and to connect the first and third channels to each other, when the second valve member is in a second position. The separate liquid channels suitably open on the first plane surface of the first valve member, and the second plane surface has an open channel forming a liquid flow connection between the first and second channels, when the second valve member is in the first position, and forming a liquid flow connection between the first and third channels when the second valve member is in the second position.

Of course, the first valve member may be provided with more than three separate liquid channels, and the second valve member may be provided with more than one open channel for forming liquid flow connections between the separate liquid channels, when the second valve member is in different positions relative to the first valve member.

The valve device may further comprise an operation device adapted to displace the second valve member relative to the first valve member and a motor, preferably an electric motor, for driving the operation device.

In accordance with a first embodiment of the valve device of the invention, the second plane surface of the second valve member is adapted to slide back and forth, preferably with the aid of the operation device operably connected to the second valve member. In this embodiment, the operation device may include an eccentric crankshaft and a slide connected to the crankshaft and attached to the second valve member, wherein the slide and second valve member are moved back and forth by the crankshaft, when the crankshaft rotates.

In accordance with a second embodiment of the valve device of the invention, the second plane surface of the second valve member is adapted to rotate and slide on the first plane surface of the first valve member, preferably with the aid of the operation device operably connected to the second valve member. In this second embodiment, the second valve member includes a disc and the operation device includes a drive shaft in rotational engagement with the disc. The valve device suitably includes a motor for rotating the drive shaft and a control device, preferably a remote control, for controlling the motor.

The valve device of the invention has few movable parts and can be made in a very small size, i.e., in the order of a few millimeters in length, and therefore, it is particularly suited for implantation in a human body. Where the valve device is implanted the above-described operation device and motor are also implanted and suitably controlled by a control device, preferably in the form of a remote control outside the human body. The implanted motor may be designed to be powered by wireless energy emitted outside the human body.

In accordance with a second aspect of the present invention, there is provided an apparatus for distributing a liquid in a patient's body, comprising a pump adapted to be implanted in the patient to pump the liquid, an implantable valve device adapted to direct the liquid pumped by the pump, a first valve member of the valve device including a first plane surface, and a second valve member of the valve device including a second plane surface facing and touching the first plane surface and being displaceable relative to the first valve member between different positions, the valve members including different liquid channels, wherein the valve device is operable to displace the second valve member to hydraulically connect the pump to at least one of the liquid channels in at least one of the positions.

The valve device of the apparatus may be designed in accordance with the valve device of the invention described above in connection with the first aspect of the invention.

Where the first valve member of the valve device has two liquid channels, first and second channels, the first channel may be connected to the pump and the second valve member may be adapted to connect the first and second channels to each other, when the second valve member is in the first position, and to seal the first channel and thus not connecting to the pump, when the second valve member is in the second position.

Where the first valve member has three separate liquid channels, first, second and third channels, the first channel may be connected to the pump and the second valve member may be adapted to connect the first and second channels to each other, when the second valve member is in the first position, and to connect the first and third channels to each other, when the second valve member is in the second position.

The apparatus of the invention may further comprise an operation device adapted to displace the second valve member relative to the first valve member and a motor, preferably an electric motor, for driving the operation device. Advantageously, the operation device may also operate the pump, which may be a membrane, piston, screw, gear or peristaltic pump, or any other suitable type of pump.

In accordance with a first embodiment of the apparatus of the present invention, the second plane surface of the second valve member is adapted to slide back and forth, preferably with the aid of the operation device operably connected to the second valve member. In this embodiment, the operation device may include an eccentric crankshaft and a slide connected to the crankshaft and attached to the second valve member, wherein the slide and second valve member are moved back and forth by the crankshaft, when the crankshaft rotates.

In the first embodiment of the apparatus, the pump is a membrane pump having a membrane, preferably with a metal coating or made only of metal, such as titanium or stainless steel, that is movable by the operation device. The operation device is adapted to move the membrane at a relatively high rate while moving the second valve member at a relatively low rate and to move the second valve member at a relatively high rate while moving the membrane at a relatively low rate. As a result, the power for operating the pump and valve device can be kept relatively low, since the membrane and second valve member are not moved simultaneously at a relatively high movement rate. To further reduce the necessary power for the operation of the pump and valve device, the operation device may be adapted to move the membrane while keeping the second valve member at rest and to move the second valve member while keeping the membrane at rest. In this first embodiment, the apparatus may comprise a holder, in which the operation device, pump and valve device are mounted. The holder may include an upper part, in which the operation device and valve device are mounted, and an under part, in which the pump is mounted, the upper and under parts being releasably attached to each other. As a result, the holder, operation device, pump and valve device form a compact small assembly easy to implant.

In accordance with a second embodiment of the apparatus of the present invention, the second plane surface of the second valve member is adapted to rotate and slide on the first plane surface of the first valve member, preferably with the aid of the operation device operably connected to the second valve member. In this second embodiment of the apparatus, the second valve member includes a disc and the operation device includes a drive shaft in rotational engagement with the disc.

Also in the second embodiment of the apparatus, the pump may be any type of pump, but specifically, in this example, it is a membrane pump having a membrane, preferably of metal, such as titanium, that is movable by the operation device. The operation device in this example includes a cam mechanism attached to the membrane, wherein the drive shaft is operably connected to the cam mechanism to cause the cam mechanism to move the membrane back and forth as the drive shaft rotates. In this second embodiment, the apparatus may comprise an at least substantially cylindrical housing, in which the operation device, pump and valve device are mounted. As a result, the cylindrical housing, operation device, pump and valve device form a compact small assembly easy to implant.

Advantageously, the valve device and pump are integrated to form an operable valve pump assembly, which is easy to implant in the patient. The above implantable operation device operates the valve pump assembly and the above implantable motor drives the operation device. The motor may be designed to be powered by wireless energy emitted outside the patient's body.

Generally, the apparatus comprises an energy transmission device for wireless transmission of energy from outside the patient's body to inside the patient's body for use in connection with the operation of the valve pump assembly. The energy transmission device transmits energy of a first form and the valve pump assembly is operable in response to energy of a second form. The apparatus further comprises an energy transforming device implantable in the patient for transforming the energy of the first form wirelessly transmitted by the energy transmission device into the energy of the second form, which is different from the energy of the first form.

The energy transforming device may include at least one element having a positive region and a negative region, wherein the element is capable of creating an energy field between the positive and negative regions when exposed to the energy of the first form transmitted by the energy transmission device, and the energy field produces the energy of the second form. For example, the element may include an electrical junction element capable of inducing an electric field between the positive and negative regions when exposed to the energy of the first form transmitted by the energy transmission device, whereby the energy of the second form comprises electric energy.

The energy transforming device may be adapted to transform the energy of the first form directly or indirectly into the energy of the second form, wherein the motor is powered by the energy of the second form. The valve pump assembly may be operable to perform a reversible function and the motor may be capable of reversing the function. For example, the control device may be adapted to shift polarity of the energy of the second form to reverse the motor. Preferably, the energy transforming device is adapted to directly power the motor by the transformed energy, as the energy of the second form is being transformed from the energy of the first form.

The wireless energy of the first form may include sound waves and the energy of the second form may include electric energy.

In accordance with an embodiment of the invention, the apparatus includes an energy storage device implantable in the patient for storing the energy of the second form and for supplying energy in connection with the operation of the valve pump assembly. For example, the energy storage device may include an accumulator, such as at least one capacitor, or at least one rechargeable battery, or a combination of at least one capacitor and at least one rechargeable battery.

In accordance with another embodiment of the present invention, the apparatus includes a source of energy implantable in the patient for supplying energy for the operation of the valve pump assembly, and a switch operable by the energy of the second form supplied by the energy transforming device to switch from an off mode, in which the source of energy is not in use, to an on mode, in which the source of energy supplies energy for the operation of the valve pump assembly.

The apparatus may include an implantable stabiliser for stabilising the energy of the second form. Where the energy of the second form includes electric current, the stabiliser includes at least one capacitor.

The apparatus may include implantable electrical components, which may be at least one voltage level guard.

Preferably, the energy transmission device is adapted to transmit wireless energy for direct use in connection with the operation of the valve pump assembly, as the wireless energy is being transmitted. The wireless energy may be in the form of a magnetic field or electromagnetic waves for direct power of the valve pump assembly. The energy transforming device may directly operate the valve pump assembly with the energy of the second form in a non-magnetic, non-thermal or non-mechanical manner.

The energy transforming device suitably includes at least one semiconductor type of component. The semiconductor component may include at least one element having a positive region and a negative region, wherein the element is capable of creating an energy field between the positive and negative regions when exposed to the energy of the first form transmitted by the energy transmission device, and the energy field produces the energy of the second form.

The valve pump assembly may be operable to perform a reversible function and a reversing device may be implantable in the patient to reverse the function performed by the valve pump assembly. The control device suitably controls the reversing device to reverse the function performed by the valve pump assembly. The reversing device may include hydraulic means including a valve for shifting the flow direction of a liquid flow in the hydraulic means. Alternatively, the reversing device may include a mechanical reversing device, such as a switch.

Preferably, the energy transmission device transmits energy by at least one wireless wave signal, such as an electromagnetic wave signal including one of an infrared light signal, a visible light signal, an ultra violet light signal, a laser signal, a micro wave signal, a radio wave signal, an x-ray radiation signal, and a gamma radiation signal. Alternatively, the wave signal may include a sound or ultrasound wave signal. Any one of these signal types may include a digital or analog signal, or a combination of a digital and analog signal.

The energy of the first form transmitted by the energy transmission device may include an electric, an electromagnetic or a magnetic field, or a combination thereof, which may be transmitted in pulses or digital pulses, or a combination of pulses and digital pulses by the energy transmission device. The energy transforming device suitably transforms the energy of the first form into a direct current or pulsating direct current, or a combination of a direct current and pulsating direct current. Alternatively, the energy transforming device may transform the energy of the first form into an alternating current or a combination of a direct and alternating current.

One of the energy of the first form and the energy of the second form may include magnetic energy, kinetic energy, sound energy, chemical energy, radiant energy, electromagnetic energy, photo energy, nuclear energy or thermal energy. Also, one of the energy of the first form and the energy of the second form may be non-magnetic, non-kinetic, non-chemical, non-sonic, non-nuclear or non-thermal.

Optionally, the energy transmission device may function differently from or similar to the energy transforming device.

The energy transforming device is suitably designed to be implanted subcutaneously or in the abdomen, thorax or cephalic region of the patient. Alternatively, the energy transforming device may be designed to be implanted in an orifice of the patient's body and under the mucosa or intraluminar outside the mucosa of the orifice.

Advantageously, the apparatus of the invention includes a control device, for example a microprocessor, for controlling the valve pump assembly. Preferably, the control device includes a remote control, conveniently a wireless remote control, for controlling the valve pump assembly from outside the patient's body. The wireless remote control may include at least one external signal transmitter or transceiver and at least one internal signal receiver or transceiver implantable in the patient. The wireless remote control may be adapted to transmit at least one wireless control signal, which may be a frequency, amplitude or frequency or amplitude modulated signal. The control signal may be an analog or a digital signal, or a combination of an analog and digital signal and the remote control may transmit an electromagnetic carrier wave signal for carrying the digital or analog control signal.

The control signal may be a wave signal including one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The remote control may transmit a carrier signal for carrying the control signal. The carrier signal may include digital, analog or a combination of digital and analog signals. Alternatively, the control signal may include an electric or magnetic field, or a combined electric and magnetic field.

The apparatus may include at least one sensor adapted to be implanted in the patient. The sensor may be adapted to sense at least one physical parameter of the patient and/or at least one functional parameter of a medical implant. Suitably, the control device may control the valve pump assembly in response to signals from the sensor. The control device may include an implantable internal control unit that directly controls the valve pump assembly or an external control unit outside the patient's body that controls the valve pump assembly in response to signals from the sensor.

The apparatus of the invention may include an external data communicator and an implantable internal data communicator communicating with the external data communicator, wherein the internal communicator feeds data related to the valve pump assembly back to the external data communicator or the external data communicator feeds data to the internal data communicator.

The apparatus of the present invention may be used for any application that requires a small and low power pump system. It provides special advantages when the valve pump assembly thereof is used as an implant because of its low energy consumption and small size, albeit with high pressure and volume. It may be used for different kinds of implantable hydraulic constriction devices, such as adjustable bands for treating reflux-disease, obesity, urinary incontinence, anal incontinence, and impotence. It may also be used with hydraulic penal implants, as well as with infusion-pumps for drug delivery, etc. The valve pump assembly of the apparatus may also be used for applications where liquid needs to be transported from a part of a patient's body, for example, from the thorax or the abdomen, or for treating hydrocephalus, i.e., for draining liquid from a patient's head.

The valve pump assembly may be used as an infusion pump for distributing nutrition or drugs. Infusion pumps for drug delivery must be very reliable and not deliver amount of the drug that is more than planned. Normally, such a drug delivery pump is used with an underpressure prevailing in the drug reservoir to prevent any unwanted delivery of drugs. The valve pump device of the present invention can be very reliable and have a very long lifetime without degradation.

The valve pump assembly may be used for distributing liquid from one part to another part of a human body for example:

1) Hydrocephalus: To much liquor in the brain is evacuated to the abdominal cavity. A safe long term working construction is needed.

2) Ascites: extravasal liquid in the abdomen is evacuated to the vein or lymphatic system.

3) Liquid in the thorax may be also be evacuated to the vein or lymphatic system but preferably the liquid is evacuated to the abdominal cavity.

The apparatus of the present invention may also be used in connection with hydraulically controlled implants to distribute liquid within the hydraulic implant or to distribute liquid to and from an implanted liquid reservoir of the implant. Examples of such hydraulically controlled implants are artificial spincters for occluding a body opening for treating anal incontinence, colostomy, ileostomy, jejunostomy, urine incontinence, or hernia in the cardia region. Another example is a hydraulic constriction device for forming a stoma opening in any part of the body of an obese patient, for example in the stomach or esophagus to treat obesity.

With regard to anal incontinence, colostomy, ileostomy or jejunostomi, the apparatus of the invention may be used for controlling a hydraulic implant as well as, in a large version of the valve pump assembly of the apparatus, for pumping fecal matter, which may be discharged through a stomy opening and or through the patient's normal anal canal.

The apparatus of the present invention may also be used for treating the vascular system, such as restricting or compressing any part of the vascular system to decrease blood pressure, for example to distribute blood from heart to lung (pulmonary hypertension), or for treating aneurysm.

The apparatus may be used for distributing liquid or blood to or from any blood vessel, vein or lymphatic vessel. For example, to shunt blood between the artery and vein system, or to get blood test samples.

The apparatus may also be used for supporting the heart by pumping the blood in the blood vessels, or even for replacing the heart.

In a particular embodiment of the present invention well suited for operating different kinds of implants, the second plane surface of the second valve member is adapted to slide on the first plane surface of the first valve member between a first position, in which the pump is hydraulically connected to a first channel of the liquid channels, and a second position, in which the pump is hydraulically connected to a second channel of the liquid channels. The first and second channels are adapted to be hydraulically connected to the implant in question, and the first and second plane surfaces have a smoothness such that they form a liquid seal as they touch each other. Accordingly, The particular embodiment may be used as follows:

1) The valve pump assembly may be adapted to pump liquid in a hydraulically operated urinary incontinence device adapted to be implanted in the patient's body. The valve pump assembly is able to hydraulically operate the urinary incontinence device to close and constrict the patient's urethra and/or urine bladder to prevent leakage of urine out from the body via the urethra opening, when the second valve member is in the first position, and to reverse the pump and/or valve function and open the urinary incontinence device to allow the patient to urinate, when the second valve member is in the second position.

2) The valve pump assembly may be adapted to pump liquid in a hydraulically operated anal incontinence device adapted to be implanted in the patient's body. The valve pump assembly is able to hydraulically operate the anal incontinence device to close and constrict the patient's intestine to prevent leakage of fecal matter out from the body via the normal anal opening, when the second valve member is in the first position, and to reverse the pump and/or valve function and open the anal incontinence device to allow the patient to defecate.

3) The valve pump assembly may be adapted to pump liquid in a hydraulically operated vascular treatment device adapted to be implanted in the patient's body. The valve pump assembly is able to hydraulically operate the vascular treatment device to increase constriction of a vascular aneurysm preventing future perforation of the aneurysm, when the second valve member is in the first position, and to reverse the pump and/or valve function and decrease the constriction.

4) The valve pump assembly may be adapted to pump liquid in a hydraulically operated vascular treatment device adapted to be implanted in the patient's body. The valve pump assembly is able to hydraulically operate the vascular treatment device to reduce blood pressure by increasing constriction of a vascular artery, when the second valve member is in the first position, and to reverse the pump and/or valve function and decrease the constriction.

5) The valve pump assembly may be adapted to pump liquid in a hydraulically operated drug delivery device for delivery of a drug inside the patient's body and adapted to be implanted in the patient's body. The valve pump assembly is able to hydraulically operate the drug delivery device to deliver a drug, when the second valve member is in the first position, and to prevent the drug delivery device to deliver any drug, when the second valve member is in the second position.

6. The valve pump assembly may be adapted to pump liquid in a hydraulically operated impotence treatment device including a constriction device adapted to be implanted in the patient's body. The valve pump assembly is able to hydraulically operate the constriction device to close and constrict the vascular veins or corpus cavernosa to create penile erection, when the second valve member is in the first position, and to reverse the pump and/or valve function and decrease the constriction to avoid penile erection.

7) The valve pump assembly may be adapted to pump liquid in a hydraulically operated impotence treatment device including corpus cavernosa implants adapted to be implanted in the patient's body. The valve pump assembly is able to hydraulically operate the impotence treatment device to fill the corpus cavernosa implants to create penile erection, when the second valve member is in the first position, and to reverse the pump and/or valve function and empty the implants.

8) The valve pump assembly may be adapted to pump liquid in a hydraulically operated reflux disease treatment device for constricting the cardia region, lower oesophagus or upper part of the stomach and adapted to be implanted in the patient's body. The valve pump assembly is able to hydraulically operate the reflux disease treatment device to close and constrict the cardia region, lower oesophagus or upper part of the stomach to prevent leakage of acid up into esophagus, when the second valve member is in the first position, and to reverse the pump and/or valve function and open the reflux disease treatment device, so that the patient is able to swallow food.

9) The valve pump assembly may be adapted to pump liquid in a hydraulically operated obesity treatment device for restricting the cardia region, lower oesophagus or upper part of the stomach and adapted to be implanted in the patient's body. The valve pump assembly is able to hydraulically operate the obesity treatment device to increase the restriction of the cardia region, lower oesophagus or upper part of the stomach to restrict food intake, when the second valve member is in the first position, and to reverse the pump and/or valve function and decrease the restriction of the obesity treatment device, so that the patient is able to increase food intake.

10) The valve pump assembly may be adapted to pump liquid in a hydraulically operated hydrocephalus treatment device including a liquid conduit adapted to be positioned between the liquor room in the patient's brain and the abdominal cavity. The valve pump assembly is able to hydraulically operate the hydrocephalus treatment device to distribute liquor between the liquor room in the brain and the abdominal cavity, when the second valve member is in the first position, and to prevent the hydrocephalus treatment device from distributing liquid between the liquor room in the brain and the abdominal cavity, when the second valve member is in the second position.

11) The valve pump assembly may be adapted to pump liquid in an implantable hydraulically operated ascites treatment device including a liquid conduit between the abdominal cavity and the vein and/or lymphatic system in the patient's body. The valve pump assembly is able to hydraulically operate the ascites treatment device to distribute liquid from the abdominal cavity into the vein and/or lymphatic system of the patient's body, when the second valve member is in the first position, and to prevent the ascites treatment device from distributing liquid from the abdominal cavity, when the second valve member is in the second position.

12) The valve pump assembly may be adapted to pump liquid in an implantable hydraulically operated intestinal stomy treatment device including a constriction device for constricting the patient's intestine to prevent accidental discharge of fecal matter and for releasing the intestine to allow discharge of fecal matter. The valve pump assembly is able to hydraulically operate the intestinal stomy treatment device to close and constrict the intestine to prevent leakage of fecal matter out from the body via the intestinal stomy, when the second valve member is in the first position, and to reverse the pump and/or valve function and open the intestinal stomy treatment device to allow the patient to defecate.

13) The valve pump assembly may be adapted to pump liquid in an implantable hydraulically operated intestinal disease treatment device including a constriction device for constricting the patient's intestine to prevent accidental discharge of fecal matter and for releasing the intestine to allow discharge of fecal matter, the patient being operated with reduction of intestinal length and the intestine still being connected to the normal anal outlet for discharge of fecal matter. The valve pump assembly is able to hydraulically operate the intestinal disease treatment device to close and constrict the intestine to prevent leakage of fecal matter out from the body via the anal opening, when the second valve member is in the first position, and to reverse the pump and/or valve function and open the intestinal disease treatment device to allow the patient to defecate.

14) The valve pump assembly may be adapted to pump fecal matter and to prevent accidental discharge of fecal matter and for releasing the intestine to allow discharge of fecal matter. The valve pump assembly is able to operate the intestinal disease treatment device to pump fecal matter out from the body via an intestinal stomy and/or the anal opening, when the second valve member is in the first position, and to reverse the pump and/or valve function and prevent the intestinal disease treatment device from discharging fecal matter.

15) The valve pump assembly may be adapted to be implanted in the heart or vascular system of a patient's body to help the heart to pump blood to prevent heart insufficiency. The first and second channels are adapted to connect to the patient's artery system such that the pump pumps the blood, when the second valve member is in the first position, and sucks the blood, when the second valve member is in the second position.

16. The valve pump assembly may also be able to in a similar way pump bile acid from the liver, gallbladder or connections thereto out into the intestines for example due to poor or nonexistent passage of bile acid.

The valve pump assembly may be adapted to pump bile acid from an implantable bile acid treatment device to allow discharge of bile acid from the liver, gallbladder and/or its connections into the intestine, the patient otherwise being unable to have adequate flow of bile acid, and said bile acid treatment device being able to pump bile acid from the liver, gallbladder and/or its connections into the intestine, when said second valve member is in said first position, and to prevent the bile acid treatment device from discharging of bile acid, when said second valve member is in said second position.

BRIEF DESCRIPTION OF THE DRAWINGS

FIG. 5 shows a cross-sectional view of another embodiment of the apparatus according to the present invention.

FIGS. 6 and 7 show a movable ceramic valve member and a stationary ceramic valve member, respectively, of a valve device of the embodiment of FIG. 5.

FIGS. 11–24 show the apparatus of the present invention implanted to treat various diseases.

Referring to the drawing Figures, like reference numerals designate identical or corresponding elements throughout the several Figures.

DETAILED DESCRIPTION OF THE DRAWINGS

Figure 1:
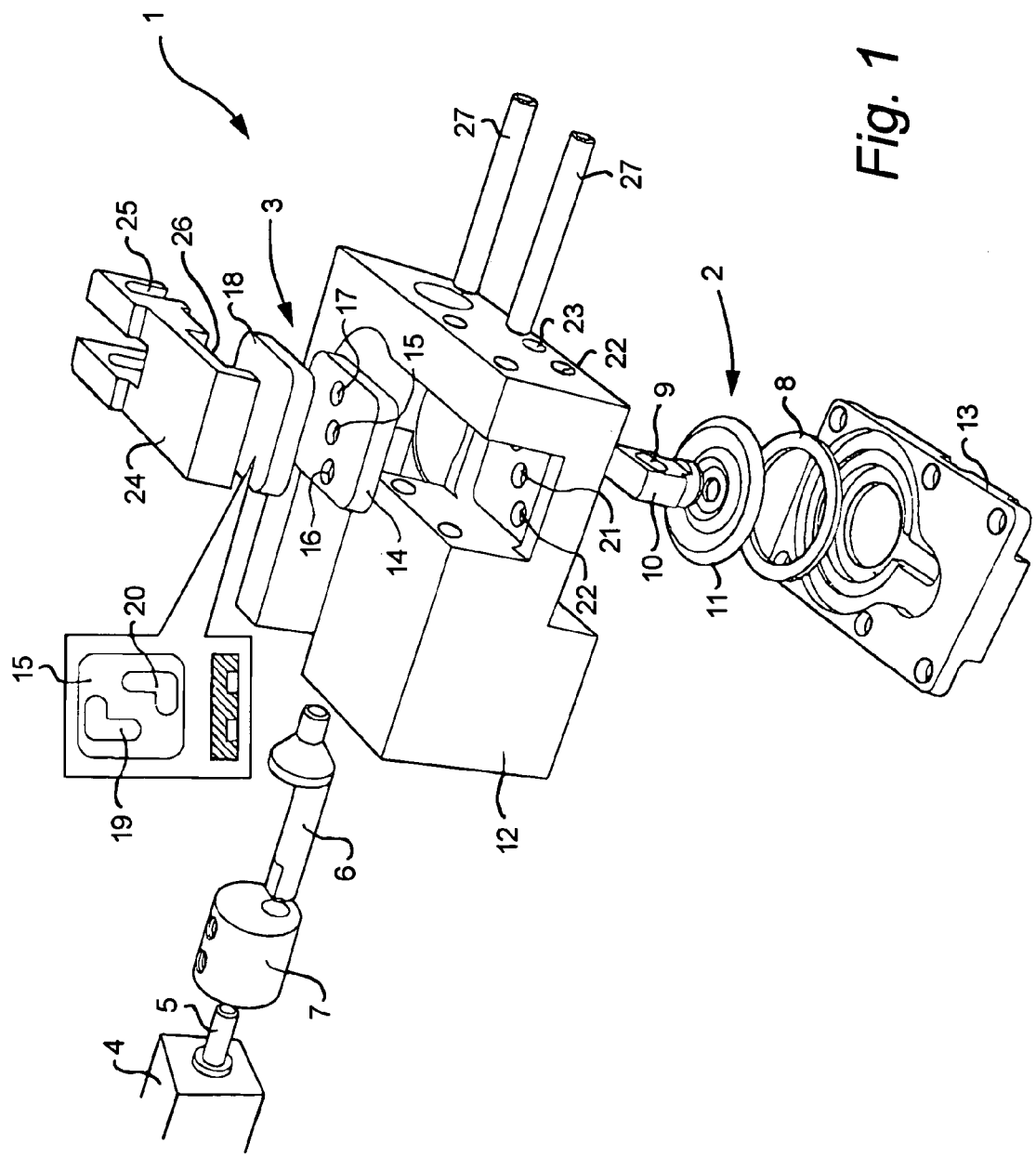
FIG. 1 shows an exploded view of an embodiment of the apparatus according to the present invention.

FIG. 1 shows an exploded view of an embodiment of the apparatus according to the present invention, comprising a valve pump assembly 1, wherein a membrane pump 2 and a valve device 3 constitute two main elements of assembly 1. Both valve device 3 and pump 2 are driven by a motor 4, which has a motor spindle 5. An operation device comprises a crankshaft 6, an eccentric connector 7 connecting motor spindle 5 and crankshaft 6, and a membrane support rod 10 having a hole 9 through which crankshaft 6 extends. Hole 9 is longitudinally extended to allow movement of eccentric crankshaft 6 therein without laterally moving support rod 10. Thus, eccentric movements of crankshaft 6 cause membrane support rod 10 to move up and down. Membrane support rod 10 is connected to a circular membrane 11 of pump 2, so that membrane 11, in turn, moves up and down, thus causing displacement movement in pump 2. Membrane 11 is mounted in a two-part metallic holder including an upper part 12, which is also the holder of valve device 3, and an under part 13. Under part 13 of the metallic holder has as a sealing rubber or plastic O-ring 8 to form a sealed cavity below membrane 11. Membrane 11 is constructed in such a way as to allow displacement movements, even though membrane 11 is rigidly mounted at its periphery.

Figure 2:
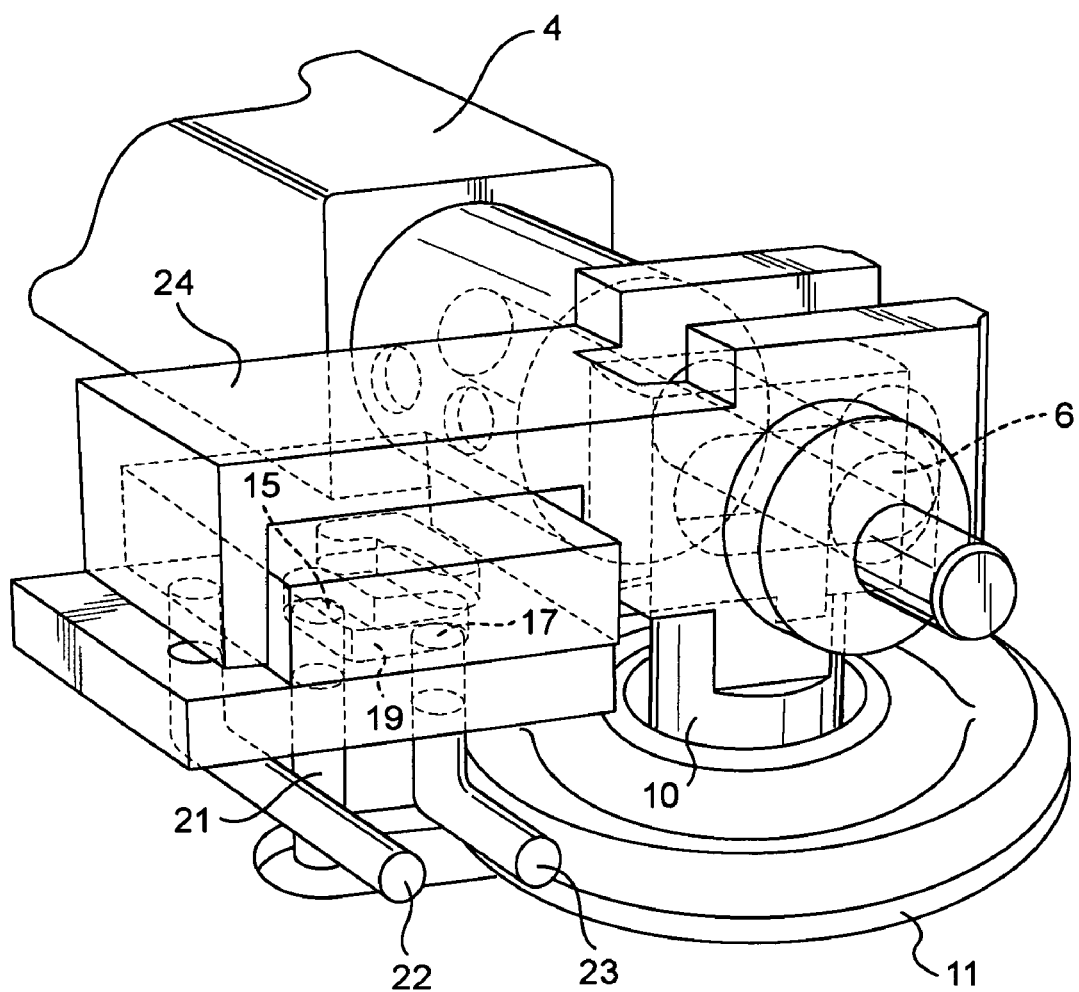
FIGS. 2–4 show views of the embodiment of FIG. 1 in three different operating positions, respectively, with some parts removed to improve clarity.
Figure 4:
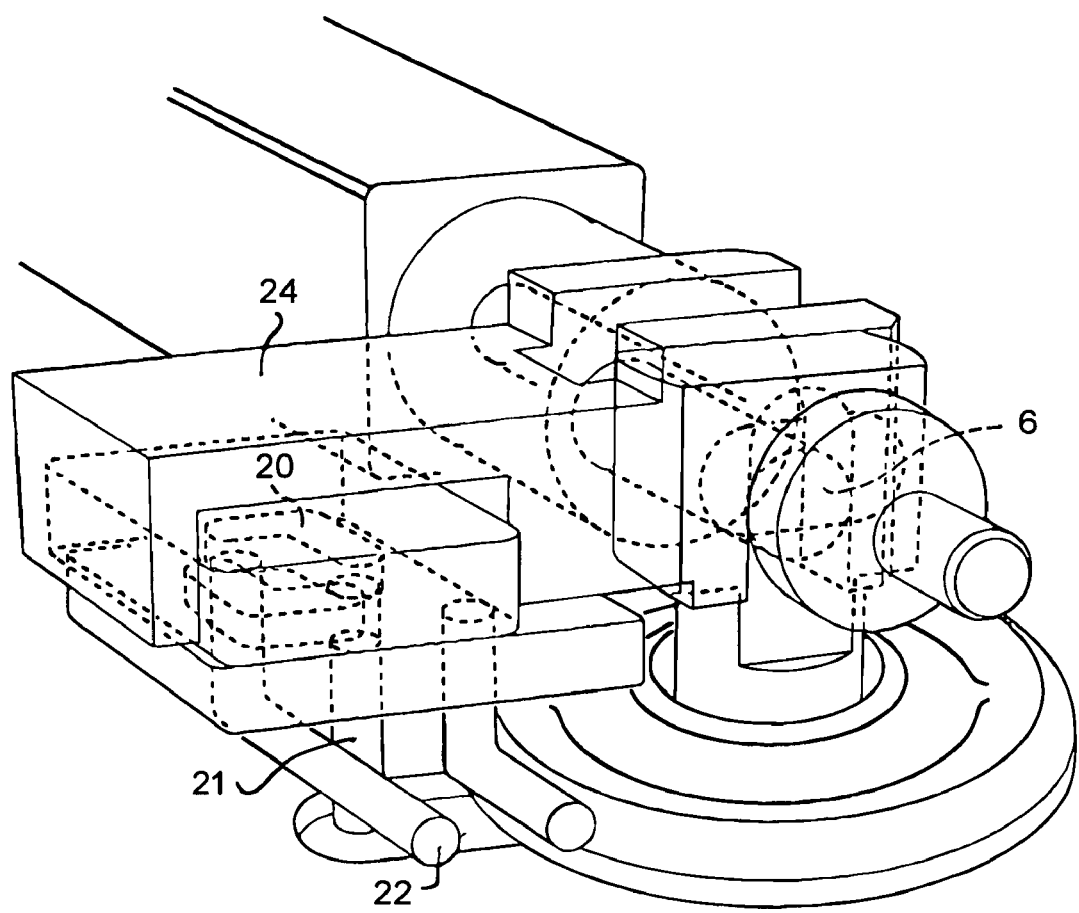

The valve device 3 of the present invention comprises a first valve member in the form of a lower ceramic plate 14 with three holes, a center hole 15, a left hole 16 and a right hole 17 in it, and a second valve member in the form of an upper ceramic plate 18, which has two angle-shaped grooves 19 and 20 forming two open channels underneath. Upper plate 18 slides back and forth on under plate 14 between two end positions, a right end position illustrated in FIG. 2 and a left end position illustrated in FIG. 4. Centre hole 15 in upper ceramic plate 18 connects to either left hole 16, as shown in FIG. 4, or right hole 17, as shown in FIG. 2, in lower plate 14, depending on the position of upper ceramic plate 18 in relation to lower ceramic plate 14. In upper metallic holder 12, a centre channel 21 connects the cavity under membrane 11 to centre hole 15 of plate 14, a left channel 22 connects to left hole 16 of plate 14 and a right channel 23 connects to right hole 17 of plate 14.

The operation device also comprises a movement transferring device in the form of a slide 24, that controls the movement of upper ceramic plate 18. Crankshaft 6 extends through a vertically extended cut-out 25 of slide 24 that allows movement of crankshaft 6 without moving slide 24 up and down. Thus, eccentric movements of crankshaft 6 cause slide 24 to move horizontally back and forth and the movement of slide 24 is at a 90° angle to the movement of membrane support rod 10. A cut-out 26 in slide 24 leaves a space for upper ceramic plate 18 to form an integrated part of slide 24. Between upper ceramic plate 18 and slide 24 is mounted a spring (not shown). Two pins 27 extend through respective holes in upper part 12 of the holder to keep slide 24 in place.

Figure 3:
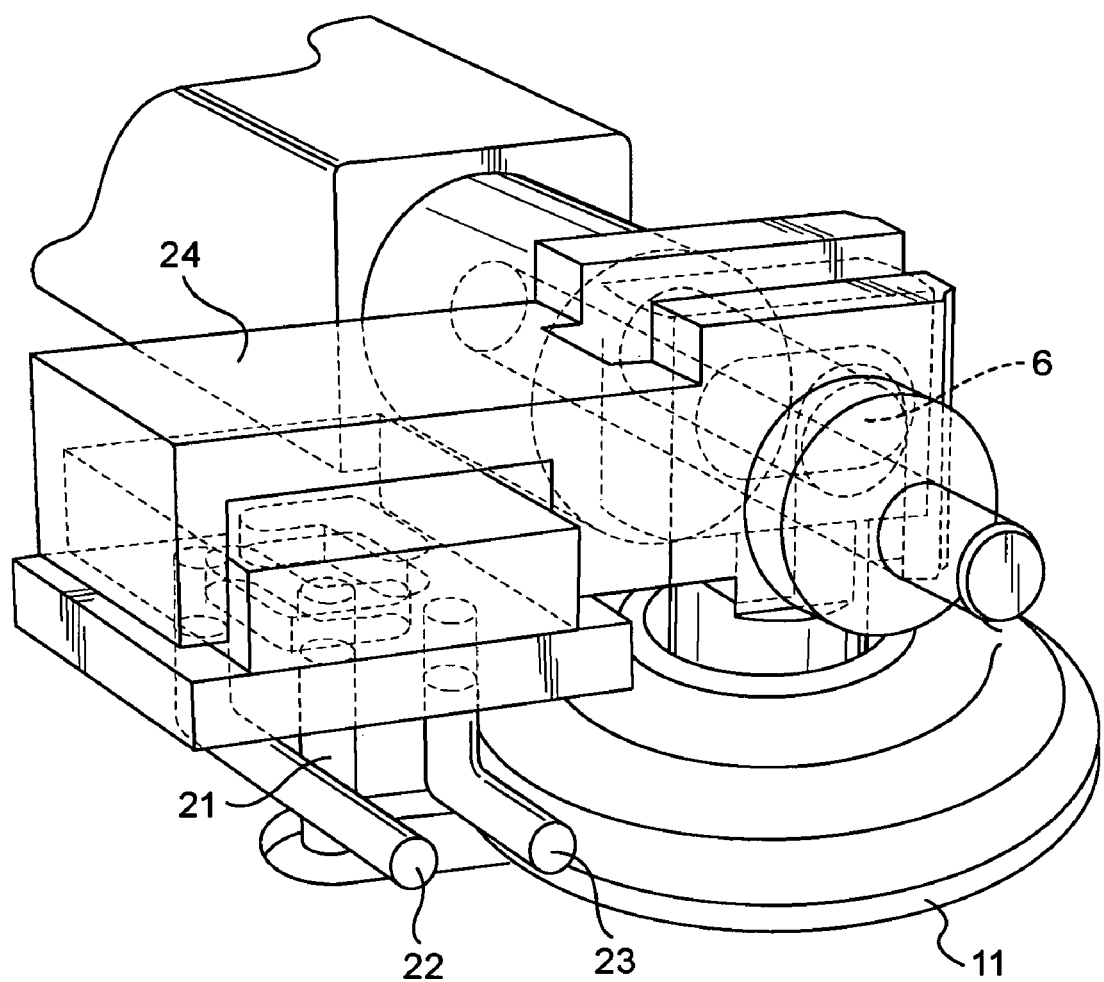

FIGS. 2–4 show the valve pump assembly 1 and the operation device of the apparatus of FIG. 1 in three different operation positions, as crankshaft 6 is rotated counter-clockwise by motor 4. Thus, FIG. 2 shows how crankshaft 6 has moved slide 24 to the right end position thereof, in which open channel 19 in upper plate 18 connects centre channel 21 to right channel 23, while crankshaft 6 moves membrane rod 10 and membrane 11 upwardly relatively fast. In this position, membrane 11 sucks liquid through channels 23, 19 and 21 into the cavity under membrane 11.

FIG. 3 shows how crankshaft 6 has rotated a quarter of a turn from the position shown in FIG. 2 to a position in which slide 24 is moved relatively fast towards its left end position, while membrane 11 has reached its upper end position. In the operation position shown in FIG. 3, center channel 21 is disconnected from both channels 22 and 23.

FIG. 4 shows how crankshaft 6 has rotated a further quarter of a turn from the position shown in FIG. 3 to a position in which slide 24 is in its left end position, while membrane 11 is moved downwardly relatively fast. In the operation position shown in FIG. 4, membrane 11 forces liquid from the cavity under it through channels 21, 20 and 22.

FIG. 5 shows a cross-sectional view of another embodiment of the apparatus according to the present invention, comprising a valve pump assembly 28, wherein a membrane pump 29 and a valve device 30 constitute two main elements of assembly 28 mounted in a cylindrical housing 31. Valve device 30 includes a first valve member in the form of a ceramic disc 32 stationary mounted on and fixed to housing 31, and a second valve member in the form of a ceramic disc 33 facing and touching ceramic disc 32 and rotatable relative to stationary disc 32. A motor 34 is mounted on housing 31 enclosing ceramic discs 32 and 33. Motor 34 includes a splined motor shaft 35 coupled to corresponding splines in an under centre hole in rotatable disc 33 to allow disc 33 to move somewhat in an axial direction relative to motor shaft 35, although disc 33 follows the rotation of motor 31. On motor shaft 35 is mounted a stop member 36 and a spring washer 37 that exerts a slight amount of pressure against disc 33 to urge it against stationary disc 32.

With reference to FIG. 6, stationary disc 32 has three holes in it that are channels, i.e., a larger centre hole that is a first channel 38, and two smaller holes, i.e., a left hole that is a second channel 40, and a right hole that is a third channel 41. Channels 40 and 41 are sealed relative to housing 31 by rubber O-rings 42 and 43, respectively. Channel 40 and 41, respectively, is connected to a channel 44 and 45, respectively, that exits from housing 31.

Figure 8:
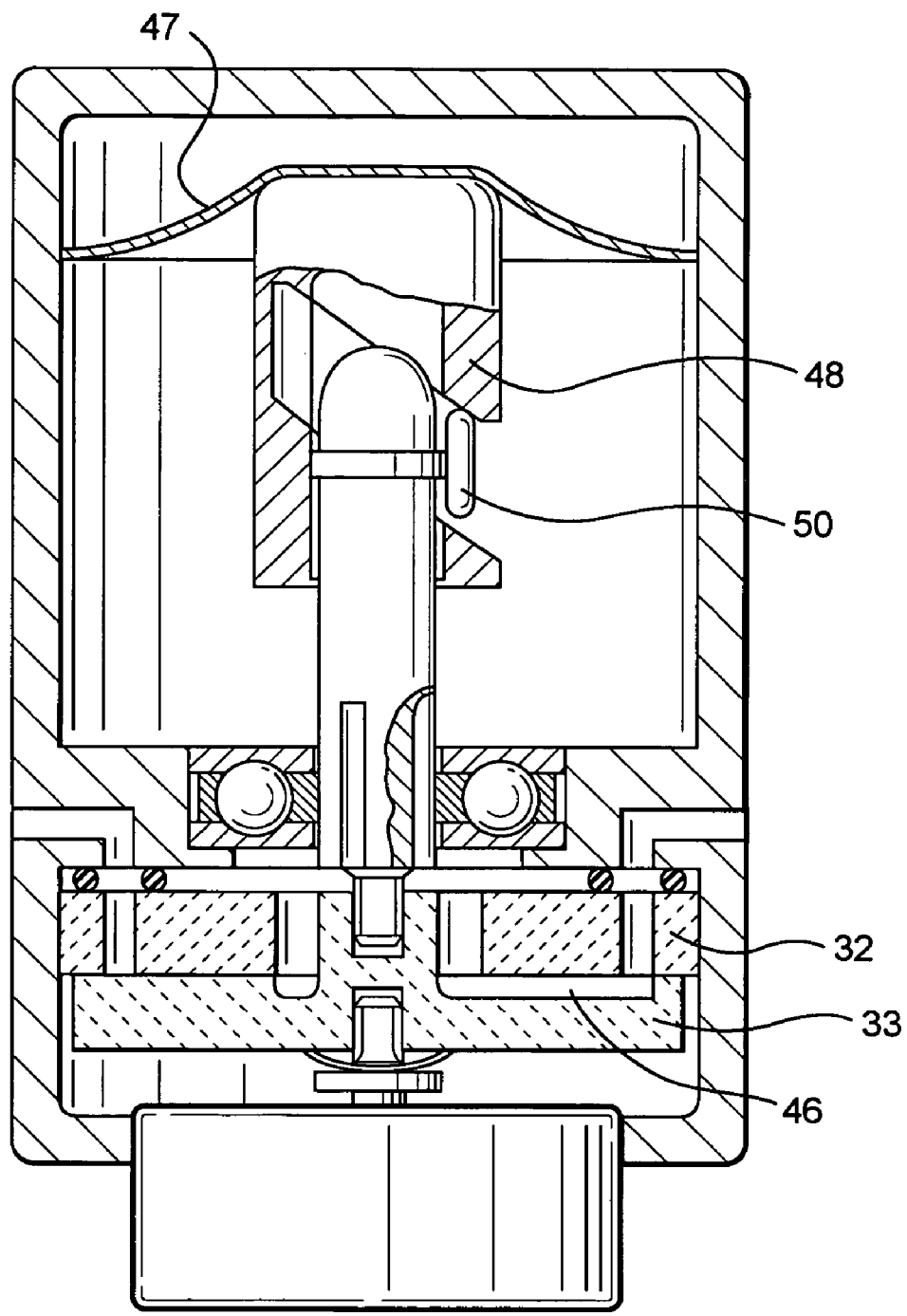
FIG. 8 shows the embodiment of FIG. 5 but at a different operating positions.

With reference to FIG. 7, rotatable disc 33 has a groove with a triangular shape that forms an open channel 46. As disc 33 rotates, open channel 46 connects either second channel 40 to first channel 38 of stationary disc 32, as shown in FIG. 5, or second channel 41 to first channel 38, as shown in FIG. 8, depending on the rotational position of rotatable disc 33.

The tolerance between rotatable disc 33 and stationary disc 32 is very fine so that no liquid is able to pass between channels 40 or 41 and 38, except through open channel 46. By using a very inert material, such as ceramic, it is possible to achieve very fine tolerances between discs 32 and 33 without such valve members sticking together over time. Ceramic works better than most metals that, when mounted together with fine tolerances between surfaces, will stick together over time.

Pump 29 includes a pump membrane 47 that can be any kind of membrane. Preferably, membrane 47 is a metal membrane, for example a titanium membrane, or a type of coated plastic material for achieving long lifetime and avoiding diffusion of liquid through membrane 47 over time. An operation device, which in this embodiment is incorporated in valve pump assembly 28, includes a cam sleeve 48, which has a cut-out groove with two opposite cam surfaces 49, a cam wheel 50, which rotates in the cut-out groove pushing against cam surfaces 49, and a pump shaft 51 connected to rotary disc 33. Cam wheel 50 is mounted via a cam wheel shaft 52 onto pump shaft 51. Pump shaft 51 rotates because it is connected to rotating disc 33 via a spline shaft 57 that is coupled to corresponding splines in an upper center hole 53 in rotatable disc 33. The described spline coupling allows disc 33 to move somewhat in an axial direction relative to pump shaft 51. Pump shaft 51 is mounted in an encapsulated ball bearing 54 and is stationary in an axial direction with respect to ball-bearing 54. Several elongated grooves 55 on pump shaft 51 extend past ball bearing 54 and serve as liquid flow passages between first channel 38 of stationary disc 32 and a pump chamber 56 under membrane 47.

Figure 9:
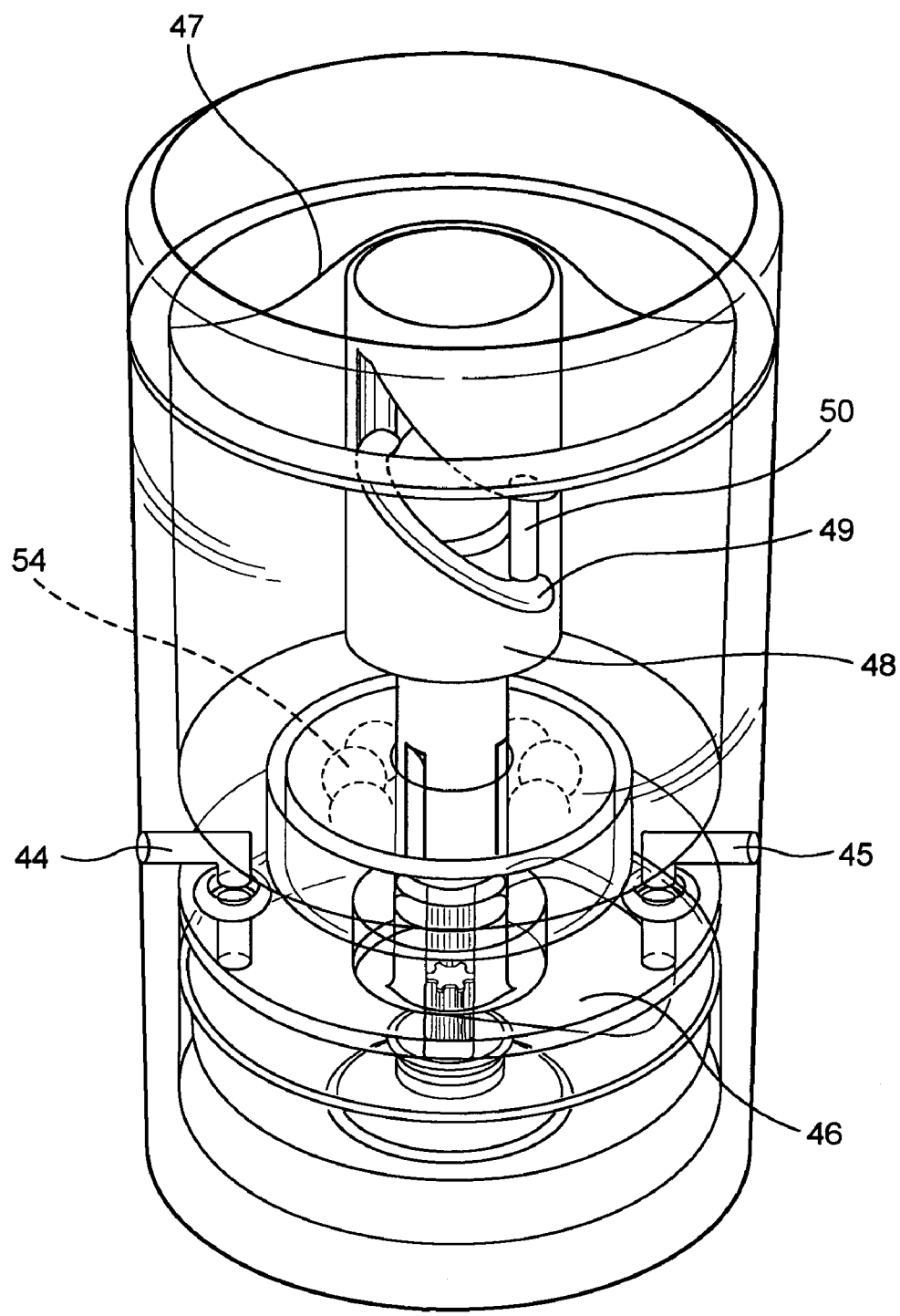
FIGS. 9 and 10 show perspective views of the embodiments of FIGS. 5 and 8, respectively, with some parts being shown as transparent.

When motor 34 is rotating, membrane 47 moves up and down. As membrane 47 moves up and down, rotatable disc 33 connects first channel 38 alternately to second and third channels 40 and 41 so that liquid is either transmitted from second channel 40 or third channel 41 to pump chamber 56 or received from pump chamber 52 by second channel 40 or third channel 41, respectively. In FIGS. 5 and 9, first channel 38 is shown as being connected to second channel 40 via open channel 46, thereby having second channel 40 receiving liquid from chamber 56. As such, in FIGS. 5 and 9 first channel 38 is shown as being connected to second channel 40 via open channel 46 so that second channel 40 receives liquid through first channel 38 from chamber 56.

Figure 10:
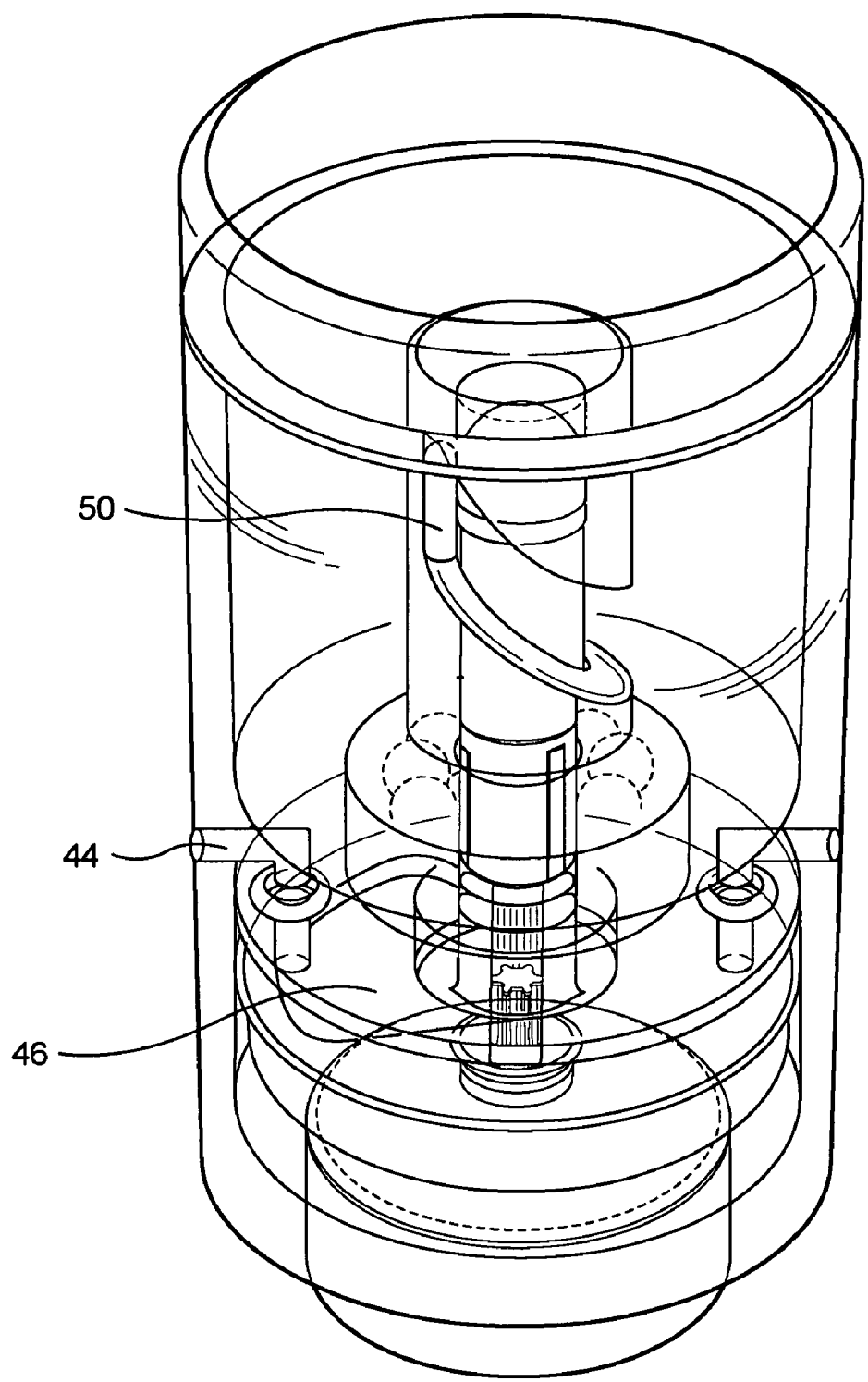

In FIGS. 8 and 10, pump shaft 51 has rotated so that membrane 47 has moved downward and, at the same time, disc 33 has rotated to connect first and second channels 38 and 40, thereby allowing third channel 41 to transmit liquid from exit channel 45 through first channel 38 to pump chamber 56.

By changing the direction of pump 29 it will be possible to change the direction of liquid flow. If necessary shaft 35 of motor 34 driving disc 33 could include a certain gap when the rotation direction is changed.

The particular material selected for discs 32 and 33 is important because the selected material must be able to function using very fine tolerances without such discs sticking to one another over time. There are several materials available on the market that would be suitable for this purpose, e.g., ceramic or ceramic mixed with other materials, such as carbon fibre.

It should also be noted that it would be possible to combine the construction principles of the different embodiments described in this application. For example, a rotating valve member arrangement like that shown in FIGS. 5–10 could be combined with the membrane moving arrangement shown in FIGS. 1–4. In addition, it is also possible to use any kind of pump construction together with the valve member construction of the present invention, either rotatable or slidable relative to one another.

FIGS. 11–24 show the apparatus of the invention implanted to treat various diseases. In all of the applications according to FIGS. 11–24, the valve device of the apparatus is designed such that the second plane surface of the second valve member slides on the first plane surface of the first valve member between a first position, in which the pump is hydraulically connected to a first channel of the liquid channels, and a second position, in which the pump is hydraulically connected to a second channel of the liquid channels. At least one of the first and second channels are hydraulically connected to the implant in question, and the first and second plane surfaces have a smoothness such that they form a liquid seal as they touch each other.

Figure 11:
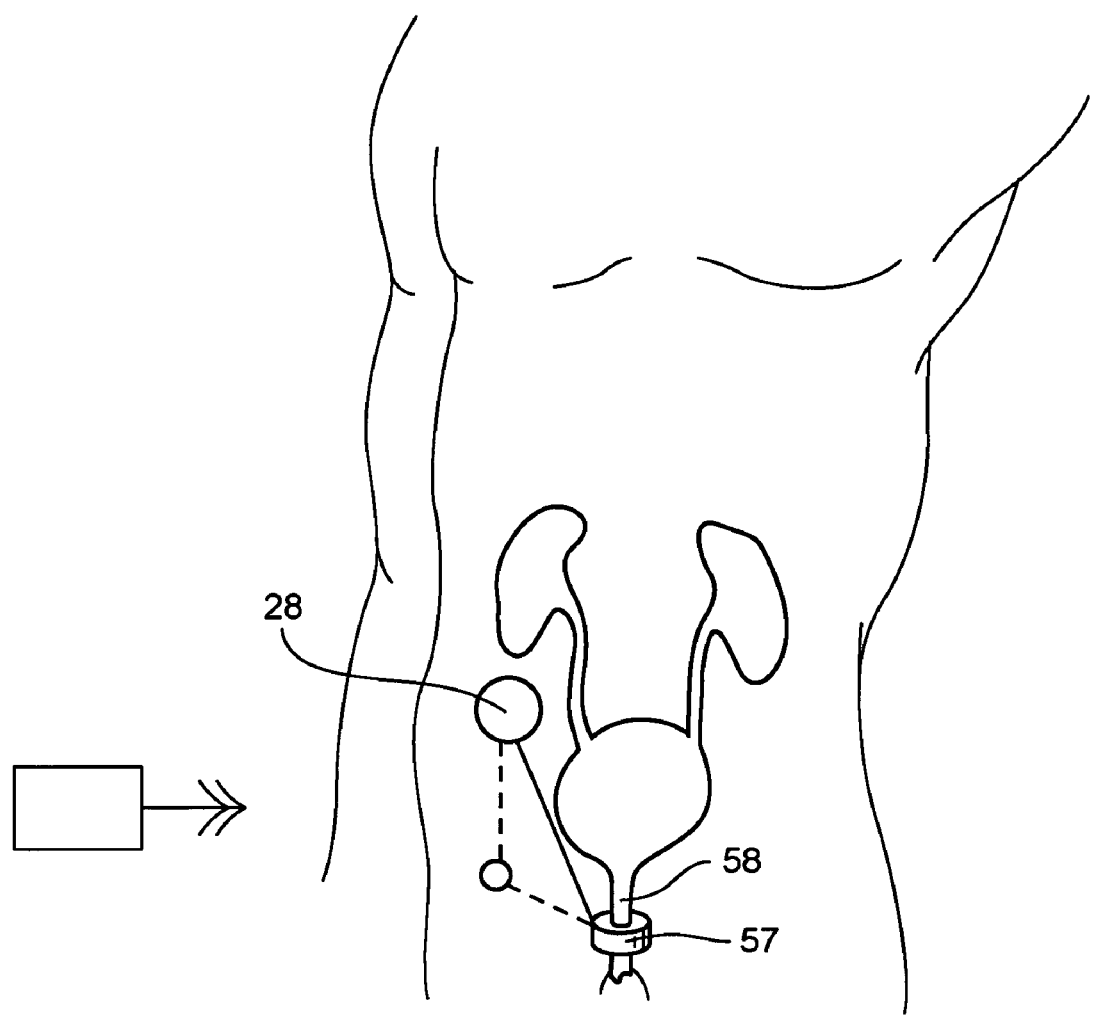

Accordingly, FIG. 11 shows how any of the above embodiments of FIGS. 1–10 is used to treat urinary incontinence. The valve pump assembly may be adapted to pump liquid in a hydraulically operated urinary incontinence device 57 adapted to be implanted in the patient's body. The valve pump assembly is able to hydraulically operate the urinary incontinence device to close and constrict the patient's urethra 58 and/or urine bladder to prevent leakage of urine out from the body via the urethra opening, when the second valve member is in the first position, and to reverse the pump and/or valve function and open the urinary incontinence device to allow the patient to urinate.

FIG. 12 shows how any of the above embodiments of FIGS. 1–10 is used to treat anal incontinence. The valve pump assembly 28 is adapted to pump liquid in a hydraulically operated anal incontinence device 59 implanted in a patient's body. The valve pump assembly is able to hydraulically operate the anal incontinence device to close and constrict the patient's intestine 60 to prevent leakage of fecal matter out from the body via the normal anal opening, when the second valve member is in the first position, and to reverse the pump and/or valve function and open the anal incontinence device to allow the patient to defecate.

FIG. 13 shows how any of the above embodiments of FIGS. 1–10 is used to treat vascular aneurysm. The valve pump assembly 28 is adapted to pump liquid in a hydraulically operated vascular treatment device implanted in a patient's body. The valve pump assembly is able to hydraulically operate the vascular treatment device to increase constriction of a vascular aneurysm preventing future perforation of the aneurysm, when the second valve member is in the first position, and to reverse the pump and/or valve function and decrease the constriction.

FIG. 14 shows how any of the above embodiments of FIGS. 1–10 is used to treat high blood pressure. The valve pump assembly 28 is adapted to pump liquid in a hydraulically operated vascular treatment device 62 implanted in a patient's body. The valve pump assembly is able to hydraulically operate the vascular treatment device to reduce blood pressure by increasing constriction of a vascular artery, when the second valve member is in the first position, and to reverse the pump and/or valve function and decrease the constriction.

Figure 15:
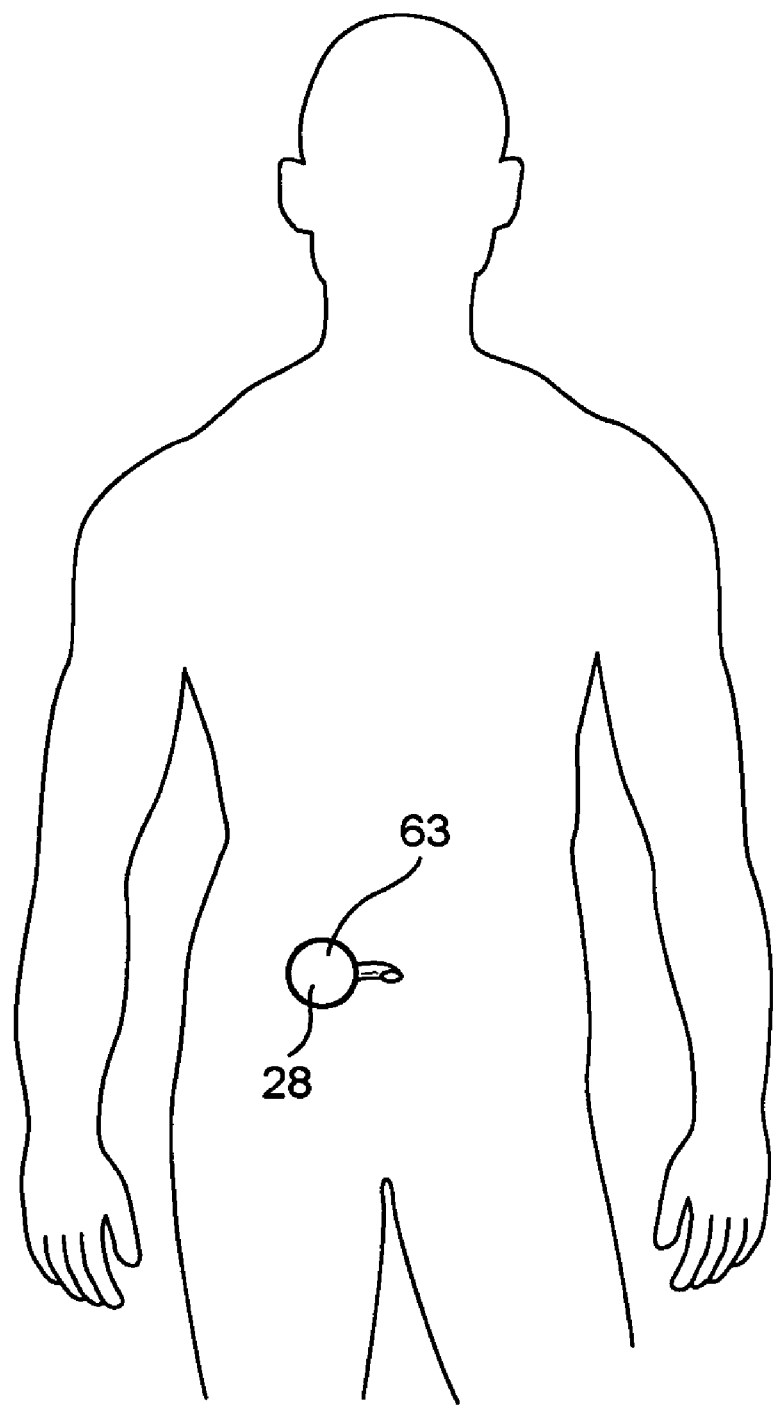

FIG. 15 shows how any of the above embodiments of FIGS. 1–10 is used to deliver a drug. The valve pump assembly is adapted to pump liquid in an implanted hydraulically operated drug delivery device 63 for delivery of a drug inside a patient's body. The valve pump assembly is able to hydraulically operate the drug delivery device to deliver drug, when the second valve member is in the first position, and to prevent the drug delivery device to deliver any drug, when the second valve member is in the second position.

Figure 16:
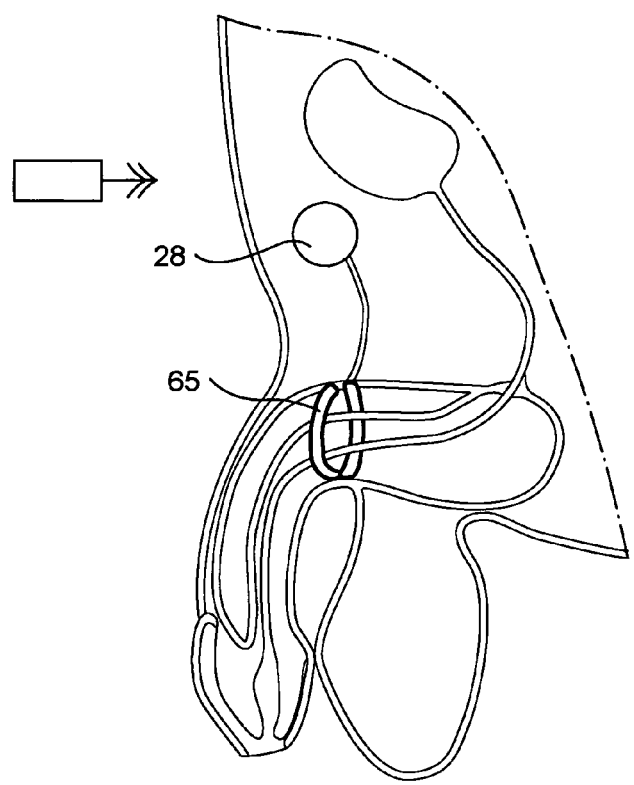

FIG. 16 shows how any of the above embodiments of FIGS. 1–10 is used to treat impotence. The valve pump assembly 28 is adapted to pump liquid in a hydraulically operated impotence treatment device 65 including a constriction device implanted in a patient's body. The valve pump assembly is able to hydraulically operate the constriction device to close and constrict the vascular veins or corpus cavernosa to create penile erection, when the second valve member is in the first position, and to reverse the pump and/or valve function and decrease the constriction to avoid penile erection.

Figure 17:
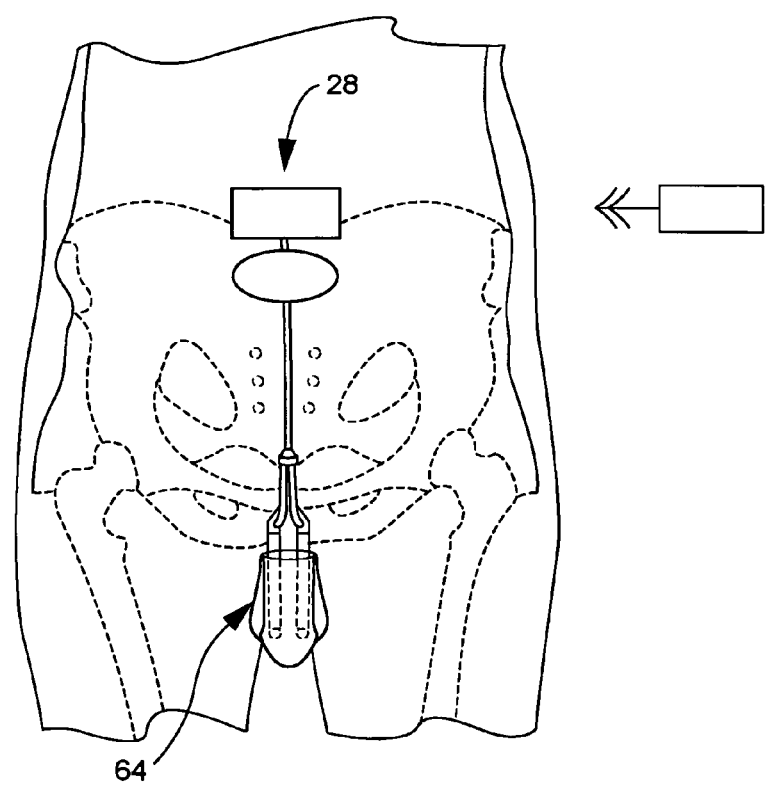

FIG. 17 shows how any of the above embodiments of FIGS. 1–10 is used to treat impotence in another way. Thus, the valve pump assembly 28 is adapted to pump liquid in a hydraulically operated impotence treatment device 64 including corpus cavernosa implants implanted in a patient's body. The valve pump assembly is able to hydraulically operate the impotence treatment device to fill the corpus cavernosa implants to create penile erection, when the second valve member is in the first position, and to reverse the pump and/or valve function and at least partly empty the implants.

Figure 18:

FIG. 18 shows how any of the above embodiments of FIGS. 1–10 is used to treat reflux disease. The valve pump assembly 28 is implanted in a patient's body and adapted to pump liquid in a hydraulically operated reflux disease treatment device 66 for constricting the cardia region, lower oesophagus or upper part of the stomach. The valve pump assembly is able to hydraulically operate the reflux disease treatment device to close and constrict the cardia region, lower oesophagus or upper part of the stomach to prevent leakage of acid up into esophagus, when the second valve member is in the first position, and to reverse the pump and/or valve function and open the reflux disease treatment device, so that the patient is able to swallow food.

Figure 19:
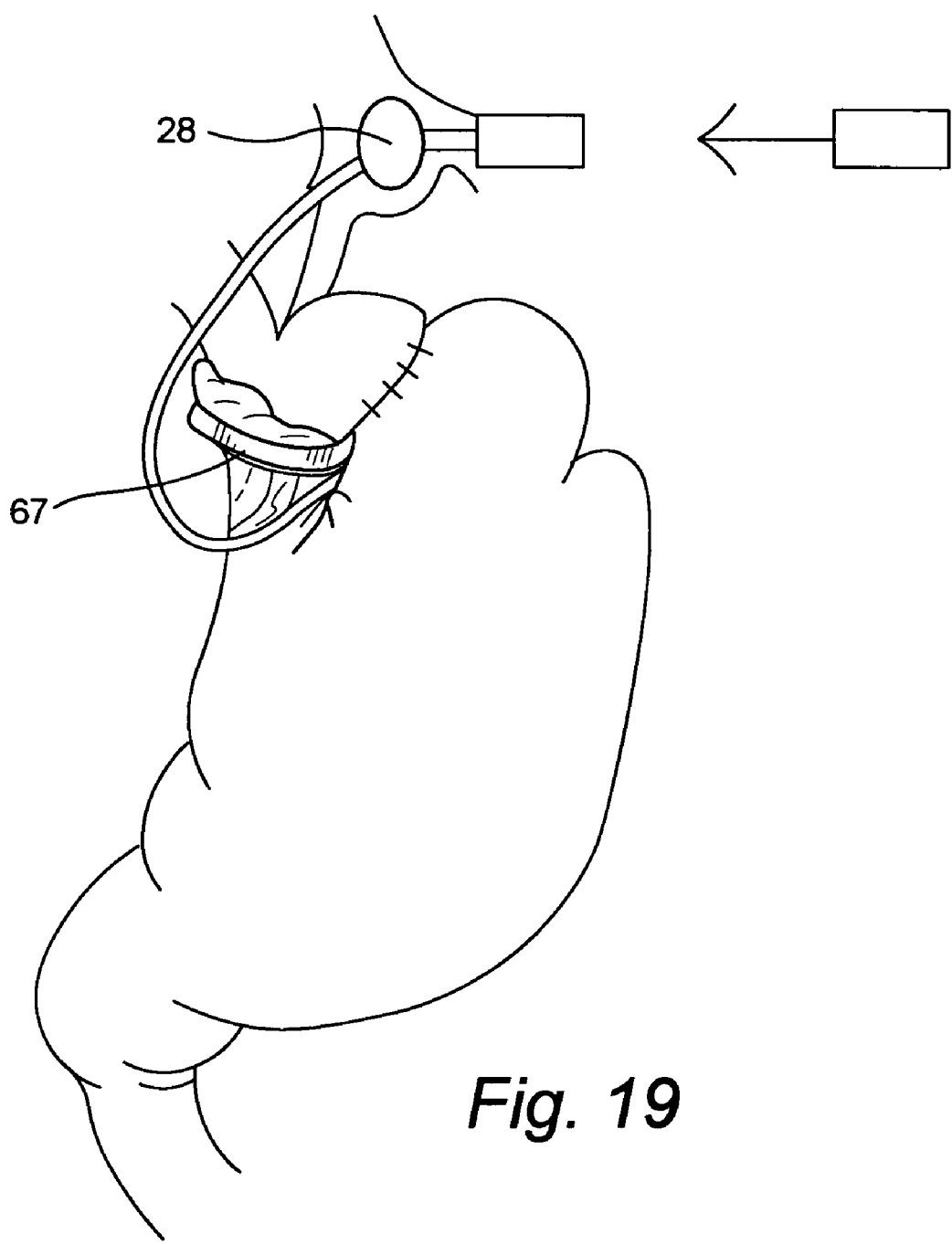

FIG. 19 shows how any of the above embodiments of FIGS. 1–10 is used to treat obesity. The valve pump assembly 28 is implanted in an obese patient's body and adapted to pump liquid in a hydraulically operated obesity treatment device 67 for restricting the cardia region, lower oesophagus or upper part of the stomach. The valve pump assembly is able to hydraulically operate the obesity treatment device to increase the restriction of the cardia region, lower oesophagus or upper part of the stomach to restrict food intake, when the second valve member is in the first position, and to reverse the pump and/or valve function and decrease the restriction of the obesity treatment device, so that the patient is able to increase food intake.

Figure 20:
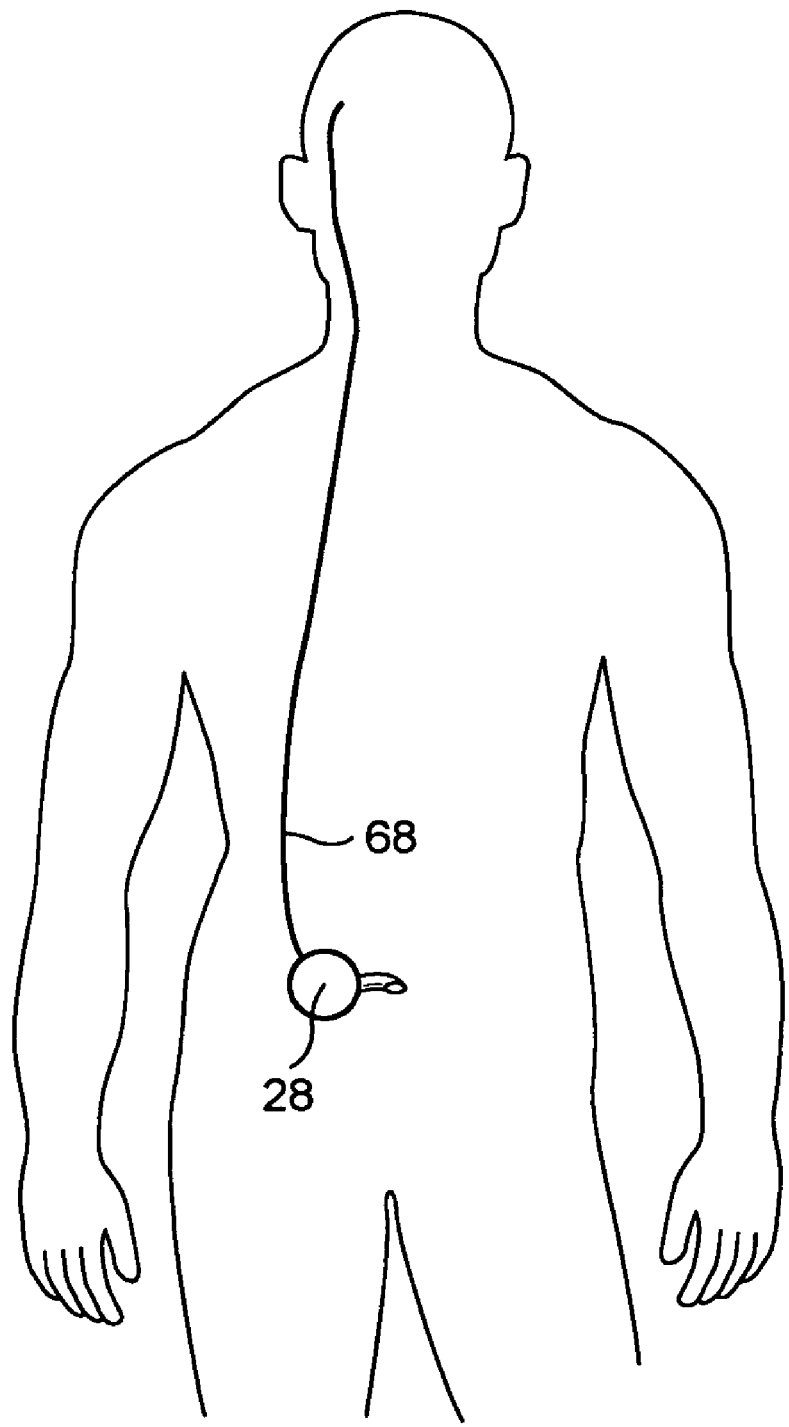

FIG. 20 shows how any of the above embodiments of FIGS. 1–10 is used to treat hydrocephalus. The valve pump assembly 28 is implanted in a patient and adapted to pump liquor in a hydraulically operated hydrocephalus treatment device including a liquid conduit adapted to be positioned between the liquor room in the patient's brain and the abdominal cavity. The valve pump assembly is able to hydraulically operate the hydrocephalus treatment device to distribute liquor between the liquid room in the brain and the abdominal cavity, when the second valve member is in the first position, and to prevent the hydrocephalus treatment device from distributing liquid between the liquid room in the brain and the abdominal cavity, when the second valve member is in the second position.

Figure 21:
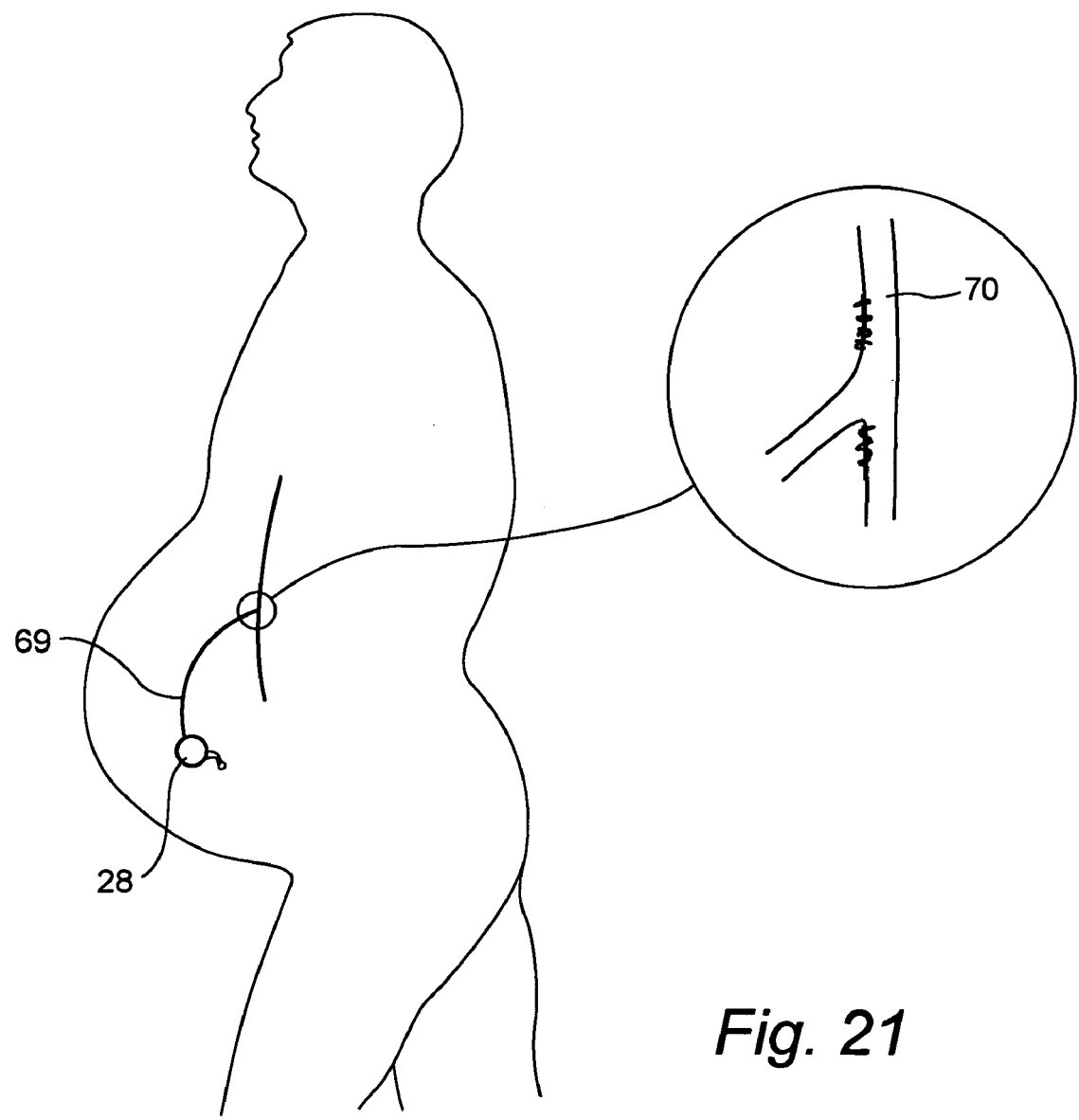

FIG. 21 shows how any of the above embodiments of FIGS. 1–10 is used to treat ascites. The valve pump assembly 28 is implanted in a patient and adapted to pump liquid in an implantable hydraulically operated ascites treatment device including a liquid conduit between the the abdominal cavity and the vein 70 and/or lymphatic system in the patient's body. The valve pump assembly is able to hydraulically operate the ascites treatment device to distribute liquid from the abdominal cavity into the vein and/or lymphatic system of the patient's body, when the second valve member is in the first position, and to prevent the ascites treatment device from distributing liquid from the abdominal cavity, when the second valve member is in the second position.

Figure 22:
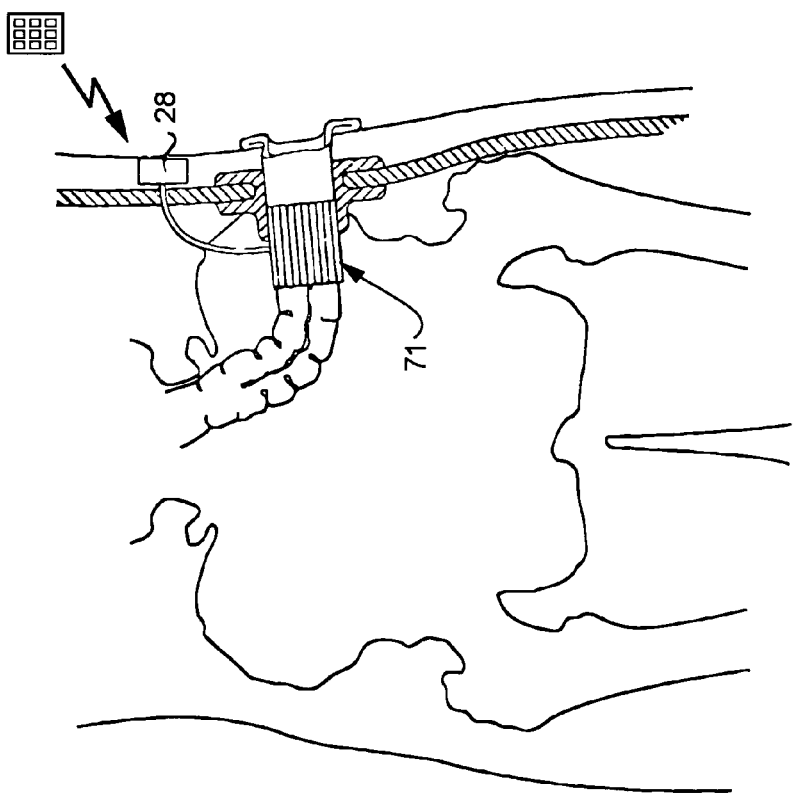

FIG. 22 shows how any of the above embodiments of FIGS. 1–10 is used to control intestinal stomy. The valve pump assembly 28 is implanted in a patient and adapted to pump liquid in an implanted hydraulically operated intestinal stomy treatment device 71 including a constriction device for constricting the patient's intestine to prevent accidental discharge of fecal matter and for releasing the intestine to allow discharge of fecal matter. The valve pump assembly is able to hydraulically operate the intestinal stomy treatment device to close and constrict the intestine to prevent leakage of fecal matter out from the body via the intestinal stomy, when the second valve member is in the first position, and to reverse the pump and/or valve function and open the intestinal stomy treatment device to allow the patient to defecate. Alternatively, the patient may be operated with reduction of intestinal length with the intestine still being connected to the normal anal outlet for discharge of fecal matter. In this alternative, the valve pump assembly may be able to hydraulically operate the intestinal treatment device to close and constrict the intestine to prevent leakage of fecal matter out from the body via the anal opening, when the second valve member is in the first position, and to reverse the pump and/or valve function and open the intestinal treatment device to allow the patient to defecate.

Figure 23:
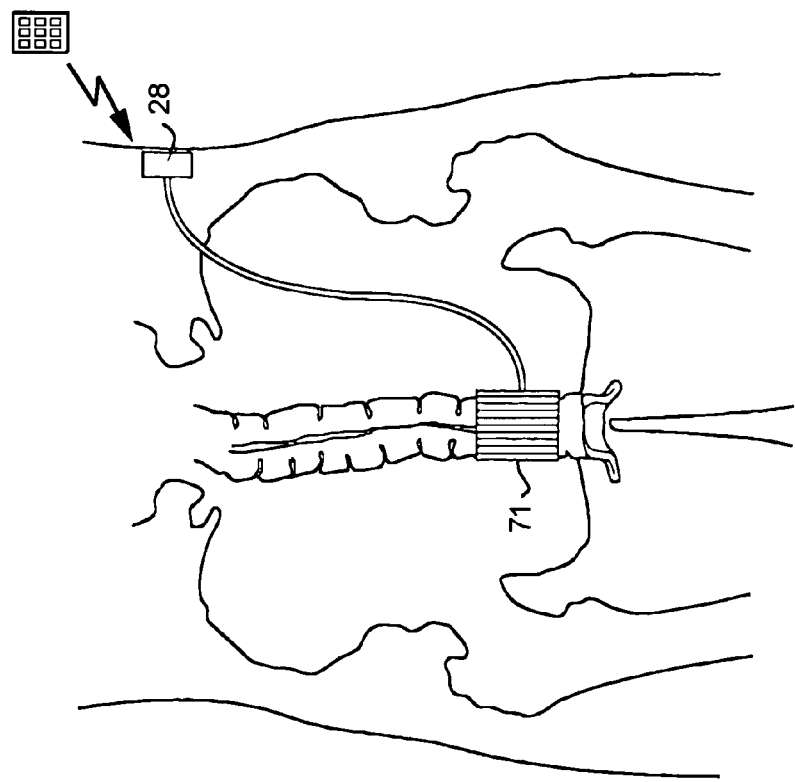

FIG. 23 shows how any of the above embodiments of FIGS. 1–10 is used to control intestinal stomy in a manner somewhat different from the application according to FIG. 22. Thus, the valve pump assembly 28 is able to operate the intestinal treatment device 71 to pump fecal matter out from the body via an intestinal stomy and/or the anal opening, when the second valve member is in the first position, and to prevent the intestinal disease treatment device from discharging fecal matter, when the second valve member is in the second position.

Figure 24:
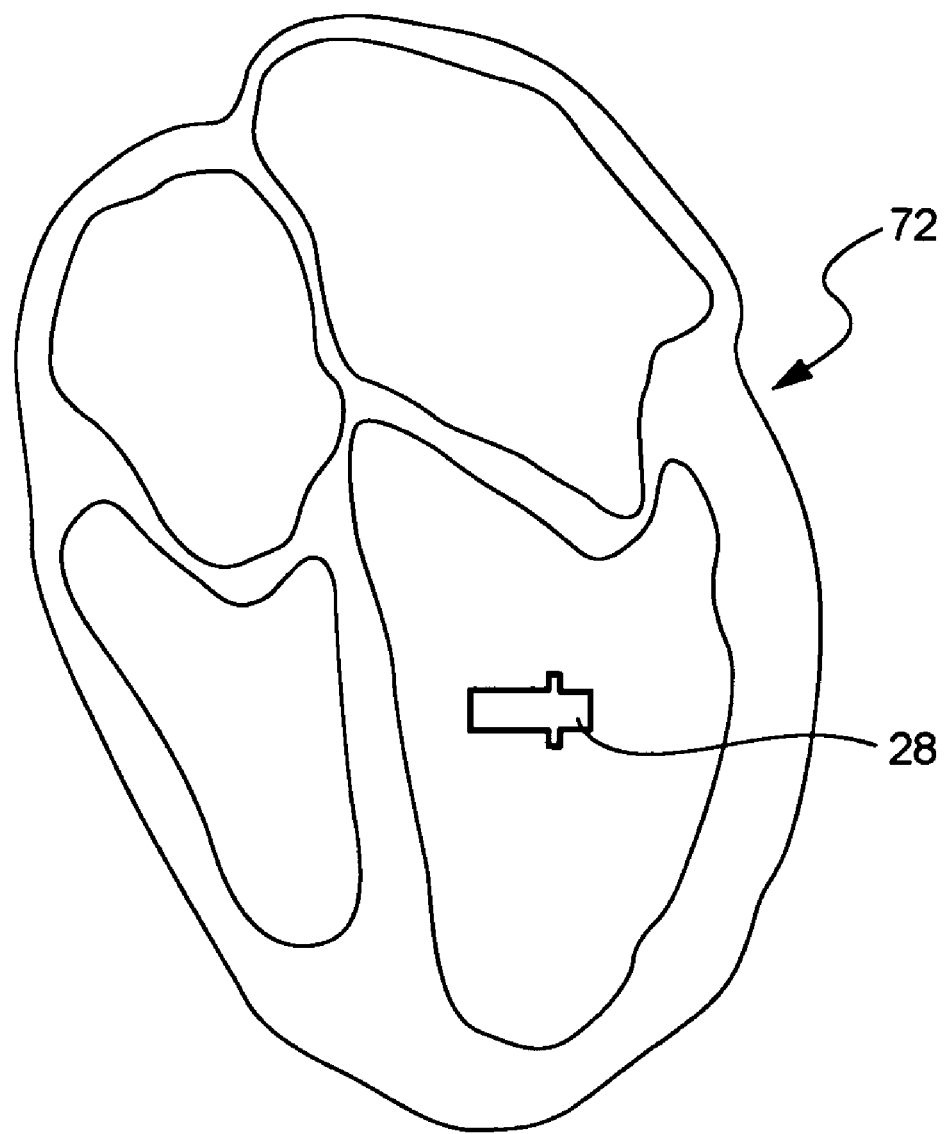

FIG. 24 shows how the above-described valve pump assembly 28 is used to help the heart 72 to pump blood to prevent heart insufficiency. The valve pump assembly is implanted in the heart or vascular system of a patient's body. The first and second channels are connected to the patient's artery system such that the pump pumps the blood, when the second valve member is in the first position, and sucks the blood, when the second valve member is in the second position.

What is claimed is:

1. A implantable valve device, comprising:
   a first valve member including a first plane surface, and
   a second valve member including a second plane surface facing and touching said first plane surface, said second valve member being displaceable relative to said first valve member between different positions while said second plane surface touches said first plane surface, said first and second plane surfaces of said valve members having a smoothness such that they form a liquid seal as they touch each other,
   said valve members including different liquid channels and said second valve member is adapted to connect at least two of said different channels to each other when said second valve member is in at least one of said positions, the implantable valve device being implantable in human or animal body.

2. A valve device according to claim 1, wherein said second valve member is displaceable relative to said first valve member between a first position and a second position.

3. A valve device according to claim 2, wherein said first valve member has at least two separate liquid channels including first and second channels, and said second valve member is adapted to connect said first and second channels to each other, when said second valve member is in said first position, and to seal said first channel, when said second valve member is in said second position.

4. A valve device according to claim 3, wherein said separate liquid channels open on said first plane surface of said first valve member, and said second plane surface has at least one open channel forming a liquid flow connection between said first and second channels, when said second valve member is in said first position.

5. A valve device according to claim 2, wherein said first valve member has at least three separate liquid channels including first, second and third channels, and said second valve member is adapted to connect said first and second channels to each other, when said second valve member is in said first position, and to connect said first and third channels to each other, when said second valve member is in said second position.

6. A valve device according to claim 5, wherein said separate liquid channels open on said first plane surface of said first valve member, and said second plane surface has at least one open channel forming a liquid flow connection between said first and second channels, when said second valve member is in said first position, and forming a liquid flow connection between said first and third channels when said second valve member is in said second position.

7. A valve device according to claim 1, wherein said second plane surface of said second valve member is adapted to slide on said first plane surface of said first valve member when said second valve member is displaced between said different positions.

8. A valve device according to claim 7, wherein said second plane surface of said second valve member is adapted to slide back and forth.

9. A valve device according to claim 8, further comprising an operation device for sliding said second valve member back and forth.

10. A valve device according to claim 9, wherein said operation device comprises an eccentric crankshaft and a slide connected to said crankshaft and attached to said second valve member, said slide and second valve member being moved back and forth by said crankshaft, when said crankshaft rotates.

11. A valve device according to claim 7, wherein said second plane surface of said second valve member is adapted to rotate and slide on said first plane surface of said first valve member.

12. A valve device according to claim 11, further comprising an operation device adapted to rotate said second valve member such that said second plane surface rotates and slides on said first plane surface.

13. A valve device according to claim 12, wherein said second valve member comprises a disc and said operation device comprises a drive shaft in rotational engagement with said disc.

14. A valve device according to claim 13, further comprising a motor for rotating said drive shaft.

15. A valve device according to claim 14, further comprising a control device for controlling said motor.

16. A valve device according to claim 1, wherein said valve members are made of a material inert enough to maintain a low friction between said first and second plane surfaces over time.

17. A valve device according to claim 16, wherein said material comprises a ceramic material.

18. A valve device according to claim 1, further comprising an operation device adapted to displace said second valve member relative to said first valve member.

19. A valve device according to claim 18, further comprising a motor for driving said operation device.

20. A valve device according to claim 19, wherein the valve device is adapted for implantation in a human body and said motor is adapted to be controlled by a remote control outside the human body.

21. A valve device according to claim 19, wherein the valve device is adapted for implantation in a human body and said motor is designed to be powered by wireless energy emitted outside the human body.

22. A valve device according to claim 18, wherein the valve device is adapted for implantation in a human body and further comprising a control device for controlling said operation device.

23. A valve device according to claim 22, wherein said control device comprises a remote control for controlling said operation device from outside the human body.

24. An implantable apparatus for distributing a liquid in a patient's body, comprising:
a pump adapted to be implanted in the patient to pump the liquid,
an implantable valve device adapted to direct the liquid pumped by said pump,
a first valve member of said valve device including a first plane surface, and
a second valve member of said valve device including a second plane surface facing and touching said first plane surface, said second valve member being displaceable relative to said first valve member between different positions while said second plane surface touches said first plane surface, said first and second plane surfaces of said valve members having a smoothness such that they form a liquid seal as they touch each other,
said valve members including different liquid channels, and said valve device is operable to displace said second valve member to hydraulically connect said pump to at least one of said liquid channels when said second valve member is in at least one of said positions.

25. An apparatus according to claim 24, wherein said second valve member is displaceable relative to said first valve member between a first position and a second position.

26. An apparatus according to claim 25, wherein said first valve member has at least two separate liquid channels including first and second channels, said first channel being connected to said pump, and said second valve member is adapted to connect said first and second channels to each other, when said second valve member is in said first position, and to seal said first channel and thus not connecting to said pump, when said second valve member is in said second position.

27. An apparatus according to claim 26, wherein said separate liquid channels open on said first plane surface of said first valve member, and said second plane surface has at least one open channel forming a liquid flow connection between said first and second channels, when said second valve member is in said first position.

28. An apparatus according to claim 25, wherein said first valve member has at least three separate liquid channels including first, second and third channels, said first channel being connected to said pump, and said second valve member is adapted to connect said first and second channels to each other, when said second valve member is in said first position, and to connect said first and third channels to each other, when said second valve member is in said second position.

29. An apparatus according to claim 28, wherein said separate liquid channels open on said first plane surface of said first valve member, and said second plane surface has at least one open channel forming a liquid flow connection between said first and second channels, when said second valve member is in said first position, and forming a liquid flow connection between said first and third channels when said second valve member is in said second position.

30. An apparatus according to claim 24, wherein said second plane surface of said second valve member is adapted to slide on said first plane surface of said first valve member when said second valve member is displaced between said different positions.

31. An apparatus according to claim 30, wherein said second plane surface of said second valve member is adapted to slide back and forth.

32. An apparatus according to claim 30, wherein said second plane surface of said second valve member is adapted to rotate and slide on said first plane surface of said first valve member.

33. An apparatus according to claim 24, further comprising an implantable operation device adapted to operate said valve device.

34. An apparatus according to claim 33, wherein said operation device is adapted to operate said valve device such that said second plane surface of said second valve member slides back and forth on said first plane surface of said first valve member.

35. An apparatus according to claim 34, wherein said operation device comprises an eccentric crankshaft and a slide connected to said crankshaft and attached to said second valve member, said slide and second valve member being moved back and forth by said crankshaft, when said crankshaft rotates.

36. An apparatus according to claim 33, wherein said operation device also is adapted to operate said pump.

37. An apparatus according to claim 36, wherein said pump comprises a membrane pump.

38. An apparatus according to claim 37, wherein said membrane pump has a membrane that is movable by said operation device, and said operation device is adapted to move said membrane at a relatively high rate while moving said second valve member at a relatively low rate and to move said second valve member at a relatively high rate while moving said membrane at a relatively low rate.

39. An apparatus according to claim 37, wherein said membrane pump has a membrane that is movable by said operation device, and said operation device is adapted to move said membrane while keeping said second valve member at rest and to move said second valve member while keeping said membrane at rest.

40. An apparatus according to claim 33, further comprising an implantable holder, in which said operation device, pump and valve members are mounted.

41. An apparatus according to claim 40, wherein said holder comprises an upper part, in which said operation device and valve members are mounted, and an under part, in which said pump is mounted, said upper and under parts being releasably attached to each other.

42. An apparatus according to claim 33, wherein said operation device is adapted to operate said valve device such that said second plane surface of said second valve member rotates and slides on said first plane surface of said first valve member.

43. An apparatus according to claim 42, wherein said second valve member comprises a disc and said operation device comprises a drive shaft in rotational engagement with said disc.

44. An apparatus according to claim 43, wherein said operation device also is adapted to operate said pump.

45. An apparatus according to claim 44, wherein said pump comprises a membrane pump.

46. An apparatus according to claim 45, wherein said membrane pump has a membrane and said operation device comprises a cam mechanism attached to said membrane, said drive shaft being operably connected to said cam mechanism to cause said cam mechanism to move said membrane back and forth as said drive shaft rotates.

47. An apparatus according to claim 42, further comprising an implantable at least substantially cylindrical housing, in which said operation device, pump and valve device are mounted.

48. An apparatus according to claim 24, wherein said pump comprises a membrane pump.

49. An apparatus according to claim 24, wherein said pump comprises a piston pump.

50. An apparatus according to claim 24, wherein said pump comprises a screw pump.

51. An apparatus according to claim 24, wherein said pump comprises a gear pump.

52. An apparatus according to claim 24, wherein said pump comprises a peristaltic pump.

53. An apparatus according to claim 24, wherein said valve members are made of a material inert enough to maintain a low friction between said first and second plane surfaces over time.

54. An apparatus according to claim 53, wherein said material comprises a ceramic material.

55. An apparatus according to claim 24, wherein said valve device and pump are integrated to form an operable valve pump assembly.

56. An apparatus according to claim 55, further comprising an implantable operation device adapted to operate said valve pump assembly.

57. An apparatus according to claim 56, further comprising an implantable motor for driving said operation device.

58. An apparatus according to claim 57, wherein said motor is designed to be powered by wireless energy emitted outside the patient's body.

59. An apparatus according to claim 55 further comprising an energy transmission device for wireless transmission of energy from outside the patient's body to inside the patient's body for use in connection with the operation of said valve pump assembly.

60. An apparatus according to claim 59, wherein said energy transmission device transmits energy of a first form and said valve pump assembly is operable in response to energy of a second form, and further comprising an energy transforming device implantable in the patient for transforming the energy of the first form wirelessly transmitted by said energy transmission device into the energy of the second form.

61. An apparatus according to claim 60, wherein the energy of the second form is different than the energy of the first form.

62. An apparatus according to claim 60, wherein said energy transforming device comprises at least one element having a positive region and a negative region, said element is capable of creating an energy field between said positive and negative regions when exposed to the energy of the first form transmitted by said energy transmission device, and said energy field produces the energy of the second form.

63. An apparatus according to claim 62, wherein said element comprises an electrical junction element, and said electrical junction element is capable of inducing an electric field between said positive and negative regions when exposed to the energy of the first form transmitted by said energy transmission device, whereby the energy of the second form comprises electric energy.

64. An apparatus according to claim 60, wherein said energy transforming device is adapted to transform the energy of the first form directly or indirectly into the energy of the second form.

65. An apparatus according to claim 64, further comprising an implantable motor for operating said valve pump assembly, wherein said motor is powered by the energy of the second form.

66. An apparatus according to claim 65, wherein said valve pump assembly is operable to perform a reversible function and said motor is capable of reversing said function.

67. An apparatus according to claim 65, further comprising a control device adapted to shift polarity of the energy of the second form to reverse said motor.

68. An apparatus according to claim 65, wherein said energy transforming device is adapted to directly power said motor by the transformed energy, as the energy of the second form is being transformed from the energy of the first form.

69. An apparatus according to claim 64, wherein the wireless energy of the first form comprises sound waves and the energy of the second form comprises electric energy.

70. An apparatus according to claim 60, further comprising an energy storage device implantable in the patient for storing the energy of the second form and for supplying energy in connection with the operation of said valve pump assembly.

71. An apparatus according to claim 70, wherein said energy storage device comprises an accumulator.

72. An apparatus according to claim 71, wherein said accumulator comprises at least one capacitor or at least one rechargeable battery, or a combination of at least one capacitor and at least one rechargeable battery.

73. An apparatus according to claim 60, further comprising a source of energy implantable in the patient for supplying energy for the operation of said valve pump assembly, and a switch operable by the energy of the second form supplied by said energy transforming device to switch from an off mode, in which said source of energy is not in use, to an on mode, in which said source of energy supplies energy for the operation of said valve pump assembly.

74. An apparatus according to claim 60, further comprising an implantable stabiliser for stabilising the energy of the second form.

75. An apparatus according to claim 74, wherein the energy of the second form comprises electric current and said stabiliser comprises at least one capacitor.

76. An apparatus according to claim 59, further comprising implantable electrical components including at least one voltage level guard.

77. An apparatus according to claim 59, wherein said energy transmission device is adapted to transmit wireless energy for direct use in connection with the operation of said valve pump assembly, as the wireless energy is being transmitted.

78. An apparatus according to claim 59, wherein said energy transmission device is adapted to transmit wireless energy in the form of a magnetic field or electromagnetic waves for direct power of said valve pump assembly.

79. An apparatus according to claim 60, wherein said energy transforming device directly operates said valve pump assembly with the energy of the second form in a non-magnetic, non-thermal or non-mechanical manner.

80. An apparatus according to claim 60, wherein said energy transforming device comprises at least one semiconductor type of component.

81. An apparatus according to claim 80, wherein said semiconductor component comprises at least one element having a positive region and a negative region, said element is capable of creating an energy field between said positive and negative regions when exposed to the energy of the first form transmitted by said energy transmission device, and said energy field produces the energy of the second form.

82. An apparatus according to claim 55, wherein said valve pump assembly is operable to perform a reversible function.

83. An apparatus according to claim 82, further comprising a reversing device implantable in the patient for reversing the function performed by said valve pump assembly.

84. An apparatus according to claim 83, wherein said control device controls said reversing device to reverse the function performed by said valve pump assembly.

85. An apparatus according to claim 83, wherein said reversing device comprises hydraulic means including a valve for shifting the flow direction of a liquid flow in said hydraulic means.

86. An apparatus according to claim 83, wherein said reversing device comprises a mechanical reversing device.

87. An apparatus according to claim 83, wherein said reversing device comprises a switch.

88. An apparatus according to claim 59, wherein said energy transmission device transmits energy by at least one wireless signal.

89. An apparatus according to claim 88, wherein said signal comprises a wave signal.

90. An apparatus according to claim 89, wherein said wave signal comprises an electromagnetic wave signal including one of an infrared light signal, a visible light signal, an ultra violet light signal, a laser signal, a micro wave signal, a radio wave signal, an x-ray radiation signal, and a gamma radiation signal.

91. An apparatus according to claim 89, wherein said wave signal comprises a sound or ultrasound wave signal.

92. An apparatus according to claim 88, wherein said signal comprises a digital or analog signal, or a combination of a digital and analog signal.

93. An apparatus according to claim 60, wherein the energy of the first form transmitted by said energy transmission device comprises an electric, an electromagnetic or a magnetic field, or a combination thereof.

94. An apparatus according to claim 93, wherein said electric, electromagnetic or magnetic field, or the combination thereof is transmitted in pulses or digital pulses, or a combination of pulses and digital pulses by said energy transmission device.

95. An apparatus according to claim 60, wherein said energy transforming device transforms the energy of the first form into a direct current or pulsating direct current, or a combination of a direct current and pulsating direct current.

96. An apparatus according to claim 60, wherein said energy transforming device transforms the energy of the first form into an alternating current or a combination of a direct and alternating current.

97. An apparatus according to claim 60, wherein one of the energy of the first form and the energy of the second form comprises magnetic energy, kinetic energy, sound energy, chemical energy, radiant energy, electromagnetic energy, photo energy, nuclear energy or thermal energy.

98. An apparatus according to claim 60, wherein one of the energy of the first form and the energy of the second form is non-magnetic, non-kinetic, non-chemical, non-sonic, non-nuclear or non-thermal.

99. An apparatus according to claim 60, wherein said energy transmission device functions different from said energy transforming device.

100. An apparatus according to claim 60, wherein said energy transmission device functions similar to said energy transforming device.

101. An apparatus according to claim 60, wherein said energy transforming device is designed to be implanted subcutaneously or in the abdomen, thorax or cephalic region of the patient.

102. An apparatus according to claim 60, wherein said energy transforming device is designed to be implanted in an orifice of the patient's body and under the mucosa or intraluminar outside the mucosa of the orifice.

103. An apparatus according to claim 24, further comprising at least one sensor adapted to be implanted in the patient.

104. An apparatus according to claim 103, wherein said sensor is adapted to sense at least one physical parameter of the patient.

105. An apparatus according to claim 103, wherein said sensor is adapted to sense at least one functional parameter of a medical implant.

106. An apparatus according to claim 103, further comprising a control device for controlling said valve device and pump in response to signals from said sensor.

107. An apparatus according to claim 106, wherein said control device comprises an implantable internal control unit that directly controls said valve device and pump in response to signals from said sensor.

108. An apparatus according to claim 106, wherein said control device comprises an external control unit outside said patient's body for controlling said valve device and pump in response to signals from said sensor.

109. An apparatus according to claim 55, further comprising a control device for controlling said valve pump assembly.

110. An apparatus according to claim 109, wherein said control device comprises a remote control for controlling said valve pump assembly from outside the patient's body.

111. An apparatus according to claim 110, wherein said remote control comprises a wireless remote control.

112. An apparatus according to claim 111, wherein said wireless remote control is adapted to transmit at least one wireless control signal for controlling said valve pump assembly.

113. An apparatus according to claim 112, wherein said control signal comprises a frequency, amplitude or frequency or amplitude modulated signal.

114. An apparatus according to claim 112, wherein said control signal comprises an analog or a digital signal, or a combination of an analog and digital signal.

115. An apparatus according to claim 109, wherein said control device comprises a microprocessor.

116. An apparatus according to claim 111, wherein said wireless remote control comprises at least one external signal transmitter or transceiver and at least one internal signal receiver or transceiver implantable in the patient.

117. An apparatus according to claim 112, wherein said remote control transmits a carrier signal for carrying said control signal.

118. An apparatus according to claim 117, wherein said carrier signal comprises digital, analog or a combination of digital and analog signals.

119. An apparatus according to claim 118, wherein said signals comprise wave signals.

120. An apparatus according to claim 112, wherein said control signal comprises a wave signal comprising one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

121. An apparatus according to claim 112, wherein said control signal comprises an electric or magnetic field, or a combined electric and magnetic field.

122. An apparatus according to claim 114, wherein said remote control transmits an electromagnetic carrier wave signal for carrying said digital or analog control signal.

123. An apparatus according to claim 55, further comprising an external data communicator and an implantable internal data communicator communicating with said external data communicator, wherein said internal communicator feeds data related to said valve pump assembly back to said external data communicator or said external data communicator feeds data to said internal data communicator.

124. An apparatus to claim 24, wherein said pump is adapted to pump liquid in a hydraulically operated urinary incontinence device adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the urinary incontinence device, said first and second plane surfaces have a smoothness such that they form a liquid seal as they touch each other, and said pump is able to hydraulically operate the urinary incontinence device to close and constrict the patient's urethra and/or urine bladder to prevent leakage of urine out from the body via the urethra opening, when said second valve member is in said first position, and to open the urinary incontinence device to allow the patient to urinate, when said second valve member is in said second position.

125. An apparatus to claim 24, wherein said pump is adapted to pump liquid in a hydraulically operated anal incontinence device adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the anal incontinence device, said first and second plane surfaces have a smoothness such that they form a liquid seal as they touch each other, and said pump is able to hydraulically operate the anal incontinence device to close and constrict the patient's intestine to prevent leakage of fecal matter out from the body via the normal anal opening, when said second valve member is in said first position, and to open the anal incontinence device to allow the patient to defecate, when said second valve member is in said second position.

126. An apparatus to claim 24, wherein said pump is adapted to pump liquid in a hydraulically operated vascular treatment device adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the vascular treatment device, said first and second plane surfaces have a smoothness such that they form a liquid seal as they touch each other, and said pump is able to hydraulically operate the vascular treatment device to increase constriction of a vascular anerysm preventing future perforation of the anerysm, when said second valve member is in said first position, and to decrease the constriction, when said second valve member is in said second position.

127. An apparatus to claim 24, wherein said pump is adapted to pump liquid in a hydraulically operated vascular treatment device adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the vascular treatment device, said first and second plane surfaces have a smoothness such that they form a liquid seal as they touch each other, and said pump is able to hydraulically operate the vascular treatment device to reduce blood pressure by increasing constriction of a vascular artery, when said second valve member is in said first position, and to decrease the constriction, when said second valve member is in said second position.

128. An apparatus to claim 24, wherein said pump is adapted to pump liquid in a hydraulically operated drug delivery device for delivery of a drug inside the patient's body and adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the drug delivery device, said first and second plane surfaces have a smoothness such that they form a liquid seal as they touch each other, and said pump is able to hydraulically operate the drug delivery device to deliver drug, when said second valve member is in said first position, and to prevent the drug delivery device to deliver any drug, when said second valve member is in said second position.

129. An apparatus to claim 24, wherein said pump is adapted to pump liquid in a hydraulically operated impotence treatment device including a constriction device adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the constriction device, said first and second plane surfaces have a smoothness such that they form a liquid seal as they touch each other, and said pump is able to hydraulically operate the constriction device to close and constrict the vascular veins or corpus cavernosa to create penile erection, when said second valve member is in said first position, and to decrease the constriction to avoid penile erection, when said second valve member is in said second position.

130. An apparatus to claim 24, wherein said pump is adapted to pump liquid in a hydraulically operated impotence treatment device including corpus cavernosa implants adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the constriction device, said first and second plane surfaces have a smoothness such that they touch each other, and said pump is able to hydraulically operate the impotence treatment device to fill the corpus cavernosa implants to create penile erection, when said second valve member is in said first position, and to empty the implants, when said second valve member is in said second position.

131. An apparatus to claim 24, wherein said pump is adapted to pump liquid in a hydraulically operated reflux disease treatment device for constricting the cardia region, lower oesophagus or upper part of the stomach and adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the reflux disease treatment device, said first and second plane surfaces have a smoothness such that they form a liquid seal as they touch each other, and said pump is able to hydraulically operate the reflux disease treatment device to close and constrict the cardia region, lower oesophagus or upper part of the stomach to prevent leakage of acid up into esophagus, when said second valve member is in said first position, and to open the reflux disease treatment device, so that the patient is able to swallow food, when said second valve member is in said second position.

132. An apparatus to claim 24, wherein said pump is adapted to pump liquid in a hydraulically operated obesity treatment device for restricting the cardia region, lower oesophagus or upper part of the stomach and adapted to be implanted in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said, first and second channels are adapted to be hydraulically connected to the obesity treatment device, said first and second plane surfaces have a smoothness such that they form a liquid seal as they touch each other, and said pump is able to hydraulically operate the obesity treatment device to increase the restriction of the cardia region, lower oesophagus or upper part of the stomach to restrict food intake, when said second valve member is in said first position, and to decrease the restriction of the obesity treatment device, so that the patient is able to increase food intake, when said second valve member is in said second position.

133. An apparatus to claim 24, wherein said pump is adapted to pump liquid in a hydraulically operated hydrocephalus treatment device including a liquid conduit adapted to be positioned between the liquid room in the patient's brain and the abdominal cavity, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the hydrocephalus treatment device, said first and second plane surfaces have a smoothness such that they form a liquid seal as they touch each other, and said pump is able to hydraulically operate the hydrocephalus treatment device to distribute liquid between the liquid room in the brain and the abdominal cavity, when said second valve member is in said first position, and to prevent the hydrocephalus treatment device from distributing liquid between the liquid room in the brain and the abdominal cavity, when said second valve member is in said second position.

134. An apparatus to claim 24, wherein said pump is adapted to pump liquid in an implantable hydraulically operated ascites treatment device including a liquid conduit between the abdominal cavity and the vein and/or lymphatic system in the patient's body, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the ascites treatment device, said first and second plane surfaces have a smoothness such that they form a liquid seal as they touch each other, and said pump is able to hydraulically operate the ascites treatment device to distribute liquid from the abdominal cavity into the vein and/or lymphatic system of the patient's body, when said second valve member is in said first position, and to prevent the ascites treatment device from distributing liquid from the abdominal cavity, when said second valve member is in said second position.

135. An apparatus to claim 24, wherein said pump is adapted to pump liquid in an implantable hydraulically operated intestinal stomy treatment device including a constriction device for constricting the patient's intestine to prevent accidental discharge of fecal matter and for releasing the intestine to allow discharge of fecal matter, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the intestinal stomy treatment device, said first and second plane surfaces have a smoothness such that they form a liquid seal as they touch each other, and said pump is able to hydraulically operate the intestinal stomy treatment device to close and constrict the intestine to prevent leakage of fecal matter out from the body via the intestinal stomy, when said second valve member is in said first position, and to open the intestinal stomy treatment device to allow the patient to defecate, when said second valve member is in said second position.

136. An apparatus to claim 24, wherein said pump is adapted to pump liquid in an implantable hydraulically operated intestinal disease treatment device including a constriction device for constricting the patient's intestine to prevent accidental discharge of fecal matter and for releasing the intestine to allow discharge of fecal matter, the patient being operated with reduction of intestinal length and the intestine still being connected to the normal anal outlet for discharge of fecal matter, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the intestinal disease treatment device, said first and second plane surfaces have a smoothness such that they form a liquid seal as they touch each other, and said pump is able to hydraulically operate the intestinal disease treatment device to close and constrict the intestine to prevent leakage of fecal matter out from the body via the anal opening, when said second valve member is in said first position, and to open the intestinal disease treatment device to allow the patient to defecate, when said second valve member is in said second position.

137. An apparatus to claim 24, wherein said pump is adapted to pump liquid in an implantable hydraulically operated intestinal disease treatment device including a constriction device for constricting the patient's intestine to prevent accidental discharge of fecal matter and for releasing the intestine to allow discharge of fecal matter, the patient being operated with reduction of intestinal length and the intestine being connected to either the normal anal outlet for discharge of fecal matter and/or the intestine being connected to a stomy outlet for discharge of fecal matter, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second channels are adapted to be hydraulically connected to the intestinal disease treatment device, said first and second plane surfaces have a smoothness such that they form a liquid seal as they touch each other, and said pump is able to hydraulically operate the intestinal disease treatment device to pump fecal matter out from the body via an intestinal stomy and/or the anal opening, when said second valve member is in said first position, and to prevent the intestinal disease treatment device from discharging fecal matter, when said second valve member is in said second position.

138. An apparatus according to claim 24, wherein said pump and valve device are incorporated in a valve pump assembly adapted to be implanted in the heart or vascular system of a patient's body to help the heart to pump blood to prevent heart insufficiency, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, said first and second plane surfaces have a smoothness such that they form a liquid seal as they touch each other, and said first and second channels are adapted to connect to the patient's artery system such that said pump pumps the blood, when said second valve member is in said first position, and sucks the blood, when said second valve member is in said second position.

139. An apparatus according to claim 24, wherein said pump is adapted to pump bile acid from an implantable bile acid treatment device to allow discharge of bile acid from the liver, gallbladder and/or its connections into the intestine, the patient otherwise being unable to have adequate flow of bile acid, said second plane surface of said second valve member is adapted to slide on said first plane surface of said first valve member between a first position, in which said pump is hydraulically connected to a first channel of said liquid channels, and a second position, in which said pump is hydraulically connected to a second channel of said liquid channels, at least one of said first and second channels, and a second position, in which said pump is hydraulically connected to a second channel of said liquid channels, at least one of said first and second channels are adapted to be hydraulically connected to the bile acid treatment device, said first and second plane surfaces have a smoothness such that they form a liquid seal as they touch each other, and said bile acid treatment device being able to pump bile acid from the liver, gallbladder and/or its connections into the intestine, when said second valve member is in said first position, and to prevent the bile acid treatment device from discharging of bile acid, when said second valve member is in said second position.

\* \* \* \* \*